(12) United States Patent
Lee et al.

(10) Patent No.: US 10,227,604 B2
(45) Date of Patent: Mar. 12, 2019

(54) PLANT SYNTHESIZING HYPOALLERGENIC PAUCIMANNOSE TYPE N-GLYCAN AND USES THEREOF

(71) Applicant: INDUSTRY-ACADEMIC COOPERATION FOUNDATION GYEONGSANG NATIONAL UNIVERSITY, Gyeongsangnam-do (KR)

(72) Inventors: Kyun Oh Lee, Gyeongsangnam-do (KR); Jae Yong Yoo, Gyeongsangnam-do (KR); Ki Seong Ko, Gyeongsangnam-do (KR); Sang Yeol Lee, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 6 days.

(21) Appl. No.: 15/420,766

(22) Filed: Jan. 31, 2017

(65) Prior Publication Data
US 2017/0137837 A1    May 18, 2017

Related U.S. Application Data

(63) Continuation-in-part of application No. PCT/KR2015/002464, filed on Mar. 13, 2015.

(30) Foreign Application Priority Data

Aug. 4, 2014 (KR) .................. 10-2014-0100010

(51) Int. Cl.
| | |
|---|---|
| C12N 15/82 | (2006.01) |
| A01H 5/00 | (2018.01) |
| C07K 14/415 | (2006.01) |
| C12N 9/10 | (2006.01) |
| A61K 38/00 | (2006.01) |

(52) U.S. Cl.
CPC ........... C12N 15/8257 (2013.01); A01H 5/00 (2013.01); C07K 14/415 (2013.01); C12N 9/1051 (2013.01); C12Y 204/01065 (2013.01); C12Y 204/01068 (2013.01); C12Y 204/01143 (2013.01); C12Y 204/02038 (2013.01); A61K 38/00 (2013.01)

(58) Field of Classification Search
None
See application file for complete search history.

(56) References Cited

U.S. PATENT DOCUMENTS

| | | | |
|---|---|---|---|
| 4,940,838 | A | 7/1990 | Schilperoort et al. |
| 2007/0214519 | A1* | 9/2007 | Fujiyama ............ C12N 9/1051 800/288 |
| 2008/0141387 | A1 | 6/2008 | Reski et al. |

FOREIGN PATENT DOCUMENTS

| | | | | |
|---|---|---|---|---|
| EP | | 0116718 B1 | 5/1990 | |
| EP | | 0120516 B1 | 10/1991 | |
| KR | 10-2013-0125337 A | | 11/2013 | |
| WO | | 2007084922 A2 | 7/2007 | |
| WO | WO 2011/117249 A1 * | | 9/2011 | ............ C12N 9/10 |

OTHER PUBLICATIONS

Oxford Dictionary definition of "deficient"; downloaded from https://en.oxforddictionaries.com/definition/deficient in 2018 (Year: 2018).*
Strasser et al. Generation of *Arabidopsis thaliana* plants with complex N-glycans lacking beta-1,2-linked xylose and core alpha-1,3-fucose. (2004) FEBS Letters; vol. 561; pp. 132-136 (Year: 2004).*
Strasser, R. Biological significance of complex N-glycans in plants and their impact on plant physiology. (2014) Frontiers in Plant Science; vol. 5; pp. 1-6 (Year: 2014).*
Callis et al. Ubiquitin extension proteins of *Arabidopsis thaliana*. (1990) JBC; vol. 265, pp. 12486-12493 (Year: 1990).*
International Search Report for PCT/KR2015/002464.
Kalyan Rao Anumula et al., "A Comprehensive Procedure for Preparation of Partially Methylated Alditol Acetates from Glycoprotein Carbohydrates", Analytical Biochemistry, 203, p. 101-108 (1992).
Hans Bakker et al., "An antibody produced in tobacco expressing a hybrid β-1,4-galactosyltransferase is essentially devoid of plant carbohydrate epitopes", Proceedings of the National Academy of Sciences, vol. 103(20), p. 7577-7582, May 16, 2006.
Chunsheng Jin et al., "A plant-derived human monoclonal antibody induces an anti-carbohydrate immune response in rabbits", Glycobiology vol. 18(3), p. 235-241, 2008.
Hartmut H.-J. Schmidt et al., "Expression and Purification of Recombinant Human Apolipoprotein A-I in Chinese Hamster Ovary Cells", Protein Expression and Purification 10, p. 226-236, 1997.
Gary Walsh, "Biopharmaceutical benchmarks 2010", Nature Biotechnology, vol. 28(9), p. 917-924, Sep. 2010.
Stacy Lawrence, "Billion dollar babies-biotech drugs as blockbusters", Nature Biotechnology, vol. 25(4), p. 380-382, Apr. 2007.
R. Strasser et al., "Generation of *Arabidopsis thaliana* plants with complex N-glycans lacking β1,2-linked xylose and core α1, 3-linked fucose", FEBS Letters 561, p. 132-136, 2004.
Saskia R. Karg et al., "Reduction of N-lined xylose and fucose by expression of rat β1,4-N-acetylglucosaminyltransferase III in tobacco BY-2 cells depends on Golgi enzyme localization domain and genetic elements used for expression", Journal of Biotechnology, 146, p. 54-65, 2010 (Abstract is submitted).

* cited by examiner

*Primary Examiner* — Cathy Kingdon Worley
(74) *Attorney, Agent, or Firm* — The PL Law Group, PLLC

(57) ABSTRACT

The present invention relates to a plant for producing a protein containing a humanized low-mannose N-glycan, and a method for producing a protein containing a customized humanized low-mannose N-glycan using the aforementioned plant.

17 Claims, 8 Drawing Sheets
Specification includes a Sequence Listing.

FIG. 2

Ubi1P:FUT8:Ubi1 polyA gene
ggatccaattttgtaatatcccgggatatttcacaaattgaacatagactacagaatttagaaaacaaa
ctttctctctcttatctcacctttatcttttagagagaaaaagttcgatttccggttgaccggaatgtat
ctttgttttttttgttttgtaacatatttcgttttccgatttagatcggatctccttttccgttttgtcg
gaccttcttccggtttatccggatctaataatatccatcttagacttagctaagtttggatctgtttttt
ggttagctcttgtcaatcgcctcatcatcagcaagaaggtgaaatttttgacaaataaatcttagaatca
tgtagtgtctttggaccttgggaatgatagaaacgatttgttatagctactctatgtatcagaccctgac
caagatccaacaatctcataggttttgtgcatatgaaaccttcgactaacgagaagtggtctttaatga
gagagatatctaaaatgttatcttaaaagcccactcaaatctcaaggcataaggtagaaatgcaaatttg
gaaagtgggctggccttttgtggtaaaggcctgtaacctagcccaatattagcaaaaccctagacgcgt
acattgacatatataaaccgcctcctccttgtttagggtttctacgtgagagaagacgaaacacaaacc
ATGGGCCTTGGACTGGTTCCTGGCGTTGGATTATGCTCATTCTTTTTGCCTGGGGGACCTTGCTGTTTT
ATATAGGTGGTCACTTGGTACGAGATAATGACCATCCTGATCACTCTAGCCGAGAACTGTCCAAGATTCT
GGCAAAGCTTGAACGCTTAAAACAGCAGAATGAAGACTTGAGGCGAATGGCCGAATCTCTCCGGATACCA
GAAGGCCCTATTGATCAGGGGCCAGCTATAGGAAGAGTACGCGTTTAGAAGAGCAGCTTGTTAAGGCCA
AAGAACAGATTGAAAATTACAAGAAACAGACCAGAAATGGTCTGGGGAAGGATCATGAAATCCTGAGGAG
GAGGATTGAAAATGGAGCTAAAGAGCTCTGGTTTTTCCTACAGAGTGAATTGAAGAAATTAAAGAACTTA
GAAGGAAATGAACTCCAAAGACATGCAGATGAATTTCTTTTGGATTTAGGACATCATGAAAGGTCTATAA
TGACGGATCTATACTACCTCAGTCAGACAGATGGAGCAGGTGATTGGCGGGAAAAAGAGGCCAAAGATCT
GACAGAACTGGTTCAGCGGAGAATAACATATCTTCAGAATCCCAAGGACTGCAGCAAAGCCAAAAAGCTG
GTGTGTAATATCAACAAAGGCTGTGGCTATGGCTGTCAGCTCCATCATGTGGTCTACTGCTTCATGATTG
CATATGGCACCCAGCGAACACTCATCTTGGAATCTCAGAATGGCGCTATGCTACTGGTGATGGGAGAC
TGTATTTAGGCCTGTAAGTGAGACATGCACAGACAGATCTGGCATCTCCACTGGACACTGGTCAGGTGAA
GTGAAGGACAAAAATGTTCAAGTGGTCGAGCTTCCCATTGTAGACAGTCTTCATCCCCGTCCTCCATATT
TACCCTTGGCTGTACCAGAAGACCTCGCAGATCGACTTGTACGAGTGCATGGTGACCCTGCAGTGTGGTG
GGTGTCTCAGTTTGTCAAATACTTGATCCGCCCACAGCCTTGGCTAGAAAAAGAAATAGAAGAAGCCACC
AAGAAGCTTGGCTTCAAACATCCAGTTATTGGAGTCCATGTCAGACGCACAGACAAAGTGGGAACAGAAG
CTGCCTTCCATCCCATTGAAGAGTACATGGTGCATGTTGAAGAACATTTTCAGCTTCTTGCACGCAGAAT
GCAAGTGGACAAAAAAGAGTGTATTTGGCCACAGATGACCCTTCTTTATTAAAGGAGGCAAAAACAAAG
TACCCCAATTATGAATTTATTAGTGATAACTCTATTTCCTGGTCAGCTGGACTGCACAATCGATACACAG
AAAATTCACTTCGTGGAGTGATCCTGGATATACATTTCTCTCTCAGGCAGACTTCCTAGTGTGTACTTT
TTCATCCCAGGTCTGTCGAGTTGCTTATGAAATTATGCAAACACTACATCCTGATGCCTCTGCAAACTTC
CATTCTTTAGATGACATCTACTATTTTGGGGGCCAGAATGCCCACAATCAAATTGCCATTTATGCTCACC
AACCCCGAACTGCAGATGAAATTCCTATGGAACCTGGAGATATCATTGGTGTGGCTGGAAATCATTGGGA
TGCTATTCTAAAGGTGTCAACAGGAAATTGGAAGGACGGGCCTATATCCCTCCTACAAAGTTCGAGAG
AAGATAGAAACGGTCAAGTACCCCACATATCCTGAGGCTGAGAAATAActagtatcaagaatcccatctc
ttgcttgctttttttgttgtcttcccttgatagggtttgtttttcttgtttcagtgactttctatgtt
aaaagataatgtcagtaaaaggatttggttttctattattctgaatcgattacggaagattcttgcttaa
ttccaatctatacaagtatcgtgaaataatgaccgtttatgtgattaggagacgtgtttcattaataaaa
tataagatcaatacattgttagtagtgataaactatgtacaaattgtattgattgtaaaagaaacacaat
aggttcctttttttctacaatatattgtgacagactctctgttttaacgaatgaattaaatttgtcgac

PLANT SYNTHESIZING HYPOALLERGENIC PAUCIMANNOSE TYPE N-GLYCAN AND USES THEREOF

CROSS REFERENCE TO RELATED APPLICATIONS

The present application is a continuation in part application to International Application No. PCT/KR2015/002464, with an International Filing Date of Mar. 13, 2015, which claims the benefit of Korean Patent Application No. 10-2014-0100010, filed in the Korean Intellectual Property Office on Aug. 4, 2014, the entire contents of which are incorporated herein by reference.

BACKGROUND

1. Technical Field

The present invention relates to a transgenic plant for producing a protein containing hypoallergenic paucimannose-type N-glycan, which does not include $\alpha 1,3$-fucose and $\beta 1,2$-xylose residues but includes $\alpha 1,6$-fucose residue, and a method for producing a protein containing hypoallergenic paucimannose-type N-glycan by using the aforementioned transgenic plant.

2. Background Art

Remarkable progress in biotechnologies leads to industrialization of various fields including the industry of pharmaceuticals, food products, environment, agriculture, sea water, bioenergy, biological process, and measurement system. Among them, the biopharmaceutical field has the highest economic value, and by having a large-scale market all over the world, it is currently expanded at significant rate. Biopharmaceuticals are medical drugs produced using biotechnology. They include therapeutic antibodies, enzymes, hormones, vaccines and proteins for diagnosis, prophylaxis, or treatment. Examples of well-known biopharmaceutical include antibodies for inhibiting tumor necrosis factor-alpha (TNF-$\alpha$) including Remicade, Enbrel, Humira, Cimzia, Simponi, Remsima and the like, which are used for treatment of an autoimmune disease, Rituxan used for treatment of B-cell type lymphoma and leukemia, Herceptin used for treatment of HER2 receptor overexpression type breast cancer, Avastin and Lucentis used for vision therapy as antibodies for inhibiting angiogenesis, interferon (interferon $\beta 1\alpha$) used for treatment of multiple sclerosis, insulin used for treatment of a patient with diabetes, erythropoietin (EPO) for promoting erythrogenesis, and Cerezyme and Fabrazyme used for treatment of lysosomal storage disease (LSD) (Lawrence, Nat Biotechnol 25, 380-382, 2007; and Walsh, Nat Biotechnol 28, 917-924, 2010).

Most biopharmaceutical glycoproteins are currently produced by culture systems using animal cells such as Chinese hamster ovary (CHO) cells or human fibroblast cells in which human-like glycans are attached. The protein folding and post-translational modification of the animal cells are similar to those of proteins produced by a human body. Thus, production systems of biopharmaceuticals using animal cells may produce biopharmaceuticals with less side effects related to protein structure (Schmidt et al., Protein Expr Purif 10, 226-236, 1997). However, there are some reports of accidental emergence of organisms harboring infectious prion (PrP$^{Sc}$) diseases and of closure of good manufacturing practice (GMP) production facilities due to contamination by animal viral pathogens. The human embryonic kidney 293 (HEK293) and fibrosarcoma HT-1080 cell lines also have been allowed for biopharmaceutical productions recently. However, the potential contamination from human-specific viruses and latent oncogenic agents in these cell lines can also be disadvantages of using those human cell lines for biopharmaceutical productions. In order to overcome this limitation and meet the increasing demand for biopharmaceuticals development of new safe and efficient production systems is necessary. Plants are relatively safe from contamination by animal viruses and prions and it is easy to establish cell lines or lineages.

Accordingly, it has a potential of producing the biopharmaceuticals in an efficient and economically favorable way. Nevertheless, the biggest reason that production systems using plants are not commonly used is that posttranslational modifications (PTMs), especially glycosylation, are different in between plants and humans. In particular, $\beta 1,2$-xylose and $\alpha 1,3$-fucose residues, which are absent in the structure of an N-glycan of mammals, are specifically added to the glycoproteins produced in plant cells. In this regard, it has been suggested that allergic reactions may be induced when biopharmaceuticals containing such plant-specific N-glycan structure is used for a treatment of a human body (Jin et al., Glycobiology 18, 235-241, 2008). Therefore, in order to develop practical plant-based biopharmaceutical production systems efficient protein expression and purification systems, as well as strategies for systematic engineering of the glycosylation pathway, need to be established.

Beta-glucocerebrosidase containing hypoallergenic paucimannose-type N-glycan can be delivered into a lysosome based on selective endocytosis via a mannose receptor present on a surface of macrophage. According to the present invention, a plant capable of producing glycoproteins containing hypoallergenic paucimannose-type N-glycan is developed. The present invention further relates to in-plant production of N-glycan not containing any plant-specific $\alpha 1,3$-fucose and $\beta 1,2$-xylose residues but containing $\alpha 1,6$-fucose residue derived from a human body in order to avoid side effects including allergic reactions of plant-based biopharmaceuticals.

As the plant for producing the customized N-glycan developed by the present invention allows direct intracellular synthesis of hypoallergenic paucimannose-type N-glycan with Man$_3$GlcNAc[Fuc($\alpha 1,6$)]GlcNAc structure without undergoing a complex enzyme treatment process using neuraminidase, galactosidase, or hexosaminidase, which have been used for production of an existing macrophage-targeting biopharmaceutical. The present invention may significantly reduce the cost and time required for producing macrophage-targeting biopharmaceuticals.

Furthermore, because the plant for producing the customized N-glycan as developed by the present invention is safe in terms of contamination with pathogenic viruses or prions that are fatal to a human body, macrophage-targeting biopharmaceuticals can be produced in a safer way.

To prepare a plant for producing a glycoprotein having hypoallergenic paucimannose-type N-glycan structure, a glycoengineering technique including removing the activity of four glycotransferases as endogenous plant enzyme and introducing the activity of one human-derived glycotransferase is used.

In Korean Patent Application Laid-Open No. 2013-0125337, "Plant synthesizing high-mannose type N-glycan and method for producing high-mannose type N-glycan" is disclosed. Furthermore, in International Application Publication WO 2007/084922, "Compositions and methods for humanization and optimization of N-glycan in plants" is disclosed. However, the plant for synthesizing hypoallergenic paucimannose-type N-glycan as described in the present invention has never been disclosed in those literatures.

SUMMARY

Exemplary embodiments of the present invention are devised under the circumstances described above.

Specifically, according to the present invention, a transgenic plant (quadruple mutant with FUT8: qmF) having human-derived α1,6-fucosyltransferase (FUT8) introduced to quadruple mutant (qm) in which T-DNA has been inserted to the genes of core α1,3-fucosyltransferase A (FucTA), core α1,3-fucosyltransferase B (FucTB), β1,2-xylosyltransferase (XylT), and β1,2-N-acetylglucosaminyltransferase II (GnTII) resulting in impaired function of the genes. The present invention is completed by confirming production of proteins containing hypoallergenic paucimannose-type N-glycan, Man$_3$GlcNAc[Fuc(α1,6)]GlcNAc which do not include plant-specific α1,3-fucose and β1,2-xylose residues but α1,6-fucose residue, from the above qmF plant.

To solve the problems described above, the present invention provides a quadruple mutant (qm) plant which is deficient of the function of core α1,3-fucosyltransferase A (FucTA), core α1,3-fucosyltransferase B (FucTB), β1,2-xylosyltransferase (XylT), and β1,2-N-acetylglucosaminyltransferase II (GnTII). The qm plant can produce a protein containing hypoallergenic paucimannose-type N-glycan that does not include α1,3-fucose and β1,2-xylose residues.

The present invention further provides a transgenic plant for producing a protein containing hypoallergenic paucimannose-type N-glycan that does not include α1,3-fucose and β1,2-xylose residues but includes α1,6-fucose residue, in which the gene encoding human-derived α1,6-fucosyltransferase (FUT8) is inserted to the above quadruple mutant plant.

The present invention further provides a callus and a seed of the aforementioned transgenic plant.

The present invention further provides a method for producing a transgenic plant for the production of a protein containing hypoallergenic paucimannose-type N-glycan that does not include α1,3-fucose and β1,2-xylose residues but includes α1,6-fucose residue. Above-mentioned method is characterized in that it includes the following steps of:
  (1) preparing a quadruple mutant (qm) plant which is deficient of the functions of FucTA, FucTB, XylT and GnTII proteins and can produce a protein containing hypoallergenic paucimannose-type N-glycan that does not include α1,3-fucose and β1,2-xylose residues, and
  (2) transforming the quadruple mutant plant prepared in the above step (1) with a recombinant vector containing a gene encoding the human-derived α1,6-fucosyltransferase (FUT8) protein to overexpress FUT8 gene, and selecting a transgenic plant which is deficient of the functions of FucTA, FucTB, XylT and GnTII proteins but with FUT8 activity.

The present invention further provides a transgenic plant prepared by the aforementioned method for producing a protein containing hypoallergenic paucimannose-type N-glycan that does not include α1,3-fucose and β1,2-xylose residues but includes α1,6-fucose residue.

The present invention further provides a method for producing a protein containing hypoallergenic paucimannose-type N-glycan that does not include α1,3-fucose and β1,2-xylose residues but includes α1,6-fucose residue, including a step of expressing a gene encoding an exogenous glycoprotein in the aforementioned plant.

The present invention further provides a protein containing hypoallergenic paucimannose-type N-glycan that does not include α1,3-fucose and β1,2-xylose residues but includes α1,6-fucose residue, said protein being produced by the aforementioned method.

The present invention still further provides a pharmaceutical composition comprising the aforementioned protein as an active ingredient.

The plant (qmF) producing the customized hypoallergenic paucimannose-type N-glycan of the present invention can be advantageously used to manufacture glycoprotein pharmaceuticals such as β-glucocerebrosidase which is used as a therapeutic enzyme for Gaucher disease. β-glucocerebrosidase should contain N-glycan with paucimannose terminal to be delivered into macrophages.

BRIEF DESCRIPTION OF THE DRAWINGS

FIG. 2 shows Ubiquitin 1 promoter (Ubi1P): front side small letters 700-nt, α1,6-fucosyltransferase (FUT8) gene: middle capital letters 1,728-nt, and Ubiquitin 1 polyadenylation signal (Ubi1 polyA): back side small letters 370-nt sequence (SEQ ID NO: 30) of the gene construct in which human-derived α1,6-fucosyltransferase (FUT8) gene is constantly expressed under regulation of *Arabidopsis thaliana* Ubiquitin 1 promoter (Ubi1P).

In FIG. 4A, Col-0, widely-used wild type (WT) of *Arabidopsis thaliana*, and the phenotypes of qm and qmF plants are shown. In FIG. 4B, Mutations and homozygosities of the FucTA, FucTB, XylT, GnTII genes are shown according to genotyping. Polymerase Chain Reaction (PCR) is performed by using a primer pair specific to the sequences of FucTA, FucTB, XylT, GnTII genes and T-DNA. Genomic DNA of WT, qm and qmF plants were used as templates. In FIG. 4C, expression of the FucTA, FucTB, XylT, GnTII gene and human-derived FUT8 gene were confirmed by reverse transcription PCR. RNA isolated from WT, qm and qmF plants is used as a template.

DETAILED DESCRIPTION

Figure 1:
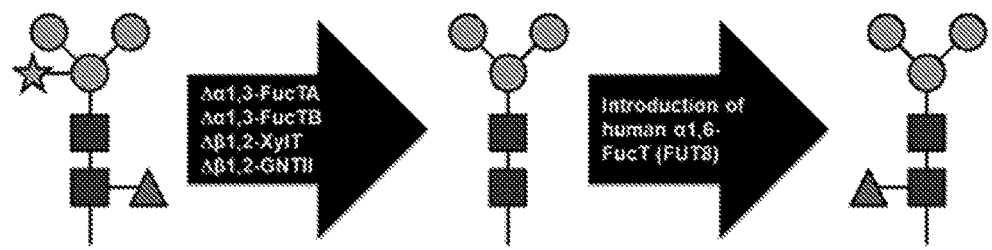
FIG. 1 show a schematic diagram illustrating the process for producing a plant (qmF) which mainly produces hypoallergenic paucimannose-type N-glycan with Man$_3$GlcNAc [Fuc(α1,6)]GlcNAc structure. Mutants in which T-DNA is inserted to genes of core α1,3-fucosyltransferase A (FucTA), core α1,3-fucosyltransferase B (FucTB), β1,2-xylosyltransferase (XylT), and β1,2-N-acetylglucosaminyltransferase II (GnTII), respectively, were selected to impair their functions. The mutants were crossed to produce a quadruple mutant (qm) which does not contain β1,2-xylose and α1,3-fucose residues that are absent in animal N-glycan but can produce a paucimannose-type N-glycan. A plant (qmF) mainly producing hypoallergenic paucimannose-type N-glycan with Man$_3$GlcNAc[Fuc(α1,6)]GlcNAc structure was produced by introducing human-derived α1,6-fucosyltransferase (FUT8) gene to the qm plant.

To achieve the object of the present invention, the present invention provides a quadruple mutant (qm) plant which is deficient of the function of core α1,3-fucosyltransferase A (FucTA), core α1,3-fucosyltransferase B (FucTB), β1,2-xylosyltransferase (XylT), and β1,2-N-acetylglucosaminyl-transferase II (GnTII) to produce a protein containing hypoallergenic paucimannose-type N-glycan that does not include α1,3-fucose and β1,2-xylose residues.

The quadruple mutant plant which is deficient of the function of FucTA, FucTB, XylT and GnTII is characterized in that part or whole nucleotide sequence of each of FucTA, FucTB, XylT and GnTII gene is removed or foreign genes including T-DNA is inserted thereto.

As for the method for deleting the function of FucTA, FucTB, XylT and GnTII, it can be a method well known in the pertinent art, namely, genome modification, gene deletion, gene insertion, T-DNA insertion, homologous recombination, transposon tagging, or the like. Preferably, it may be a method of deleting the function of the above proteins by eliminating the gene expression of FucTA, FucTB, XylT and GnTII gene in a transgenic plant group inserted with T-DNA.

Included in the scope of the FucTA, FucTB, XylT and GnTII proteins are the protein having an amino acid sequence represented by SEQ ID NOS: 2, 4, 6 and 8, respectively, and functional equivalents of the protein. As described herein, the expression "functional equivalents" means a protein which has, as a result of addition, substitution, or deletion of an amino acid, at least 70%, preferably at least 80%, more preferably at least 90%, and even more preferably at least 95% sequence homology with the amino acid sequence represented by SEQ ID NOS: 2, 4, 6 and 8, and it indicates a protein which exhibits substantially the same physiological activity as the protein represented by SEQ ID NOS: 2, 4, 6 and 8.

Furthermore, the genes encoding the FucTA, FucTB, XylT and GnTII proteins include both the genomic DNA and cDNA. Preferably, cDNA sequence of FucTA, FucTB, XylT and GnTII gene may contain a nucleotide sequence which is represented by SEQ ID NOS: 1, 3, 5 and 7, respectively. Furthermore, homologues of the nucleotide sequence are also within the scope of the present invention. Specifically, each of FucTA, FucTB, XylT and GnTII gene may comprise a nucleotide sequence which has preferably at least 70%, more preferably at least 80%, still more preferably at least 90%, and most preferably at least 95% homology with the nucleotide sequence of SEQ ID NOS: 1, 3, 5 and 7. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

The deficiency of FucTA, FucTB, XylT and GnTII function according to one embodiment of the present invention can be achieved by inserting T-DNA to each of FucTA, FucTB, XylT and GnTII gene, but it is not limited thereto.

The present invention further provides a transgenic plant for producing a protein containing hypoallergenic paucimannose-type N-glycan that does not include α1,3-fucose and β1,2-xylose residues but includes α1,6-fucose residue, in which the gene encoding human-derived α1,6-fucosyltransferase (FUT8) protein is inserted to the above quadruple mutant plant.

With regard to the plant according to one embodiment of the present invention, the modified N-glycan may be a paucimannose-type N-glycan that does not include α1,3-fucose and β1,2-xylose residues but contains α1,6-fucose residue, and it is preferably $Man_3GlcNAc[Fuc(α1,6)]GlcNAc$.

Insertion of FUT8 gene can be carried out by transformation with a recombinant vector which contains a gene encoding the human-derived α1,6-fucosyltransferase (FUT8) protein consisting of an amino acid sequence of SEQ ID NO: 10.

The above FUT8 gene includes both the genomic DNA and cDNA. Preferably, the cDNA sequence of FUT8 gene may contain a nucleotide sequence consisting of SEQ ID NO: 9.

The term "recombinant" used in the present invention indicates a cell which replicates a heterogeneous nucleotide or expresses above-mentioned nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that above-mentioned gene is modified and re-introduced into the cell by an artificial means.

The term "vector" is used herein to refer DNA fragment (s) and nucleotide molecules that are delivered to a cell. Vector can replicate DNA and be independently reproduced in a host cell. The terms "delivery system" and "vector" are often interchangeably used. The term "expression vector" means a recombinant DNA molecule comprising a desired coding sequence and other appropriate nucleotide sequences that are essential for the expression of the operatively-linked coding sequence in a specific host organism. Promoter, enhancer, termination codon and polyadenylation signal that can be used for a eukaryotic cell are well known in the pertinent art.

The recombinant vector is preferably a recombinant plant expression vector.

A preferred example of plant expression vector is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid DNA to protoplasts that can produce a new plant by appropriately inserting a plant cell or hybrid DNA to a genome of a plant. Especially preferred form of Ti-plasmid vector is a so called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of above-mentioned vector can be advantageous especially when a plant host cannot be appropriately transformed.

Expression vector would preferably comprise at least one selective marker. Above-mentioned selective marker is a nucleotide sequence having a property based on that it can be selected by a common chemical method. Every gene which can be used for the differentiation of transformed cells from non-transformed cell can be a selective marker. Example includes, a gene resistant to herbicide such as glyphosate and phosphintricin, and a gene resistant to antibiotics such as kanamycin, G418, bleomycin, hygromycin, chloramphenicol, and toxoflavin, but not limited thereto.

For the plant expression vector according to the present invention, the promoter can be any of CaMV 35S, actin, ubiquitin, pEMU, MAS or histone promoter, but not limited thereto. The term "promoter" means a DNA molecule to which RNA polymerase binds in order to initiate its transcription, and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, a constitutive promoter can be preferable for the present invention. Therefore, a possibility for choosing a constitutive promoter is not limited herein.

For the plant expression vector of the present invention, any conventional terminator can be used. Example includes, nopaline synthase (NOS), rice α-amylase RAmy1 A terminator, phaseoline terminator, a terminator for optopine gene of *Agrobacterium tumefaciens*, and *E. coli* rrn B1/B2 terminator, etc., but are not limited thereto. Regarding the necessity of terminator, it is generally known that such region can increase a reliability and an efficiency of transcription in plant cells. Therefore, the use of terminator is highly preferable in view of the contexts of the present invention.

As for the method for delivering the vector of the present invention to inside of a host cell, it can be carried out by a microinjection method, a calcium phosphate precipitation method, an electroporation method, a liposome-mediated transfection, a DEAE-dextran treatment method, a gene bombardment, or the like.

The recombinant vector according to one embodiment of the present invention is characterized in that it comprises a polynucleotide (SEQ ID NO: 30) having *Arabidopsis thaliana* ubiquitin 1 promoter, a gene encoding human-derived α1,6-fucosyltransferase (FUT8) protein which consists of an amino acid sequence of SEQ ID NO: 10, and an *Arabidopsis thaliana* ubiquitin 1 polyadenylation signal.

The plant of the present invention can be food crops, vegetable crops, special crops, fruit plants, flowers, or feed crops, and it is preferably a plant selected from the group consisting of rice, wheat, barley, corn, soybean, potato, red bean, oat, sorghum, *Arabidopsis thaliana*, Chinese cabbage, daikon, pepper, strawberry, tomato, watermelon, cucumber, cabbage, oriental melon, zucchini, scallion, onion, carrot, *ginseng*, tobacco, cotton, sesame, sugar cane, sugar beet, wild sesame, peanut, canola, apple, pear, jujube, peach, kiwi, grape, tangerine, persimmon, plum, apricot, banana, rose, *gladiolus, gerbera*, carnation, *chrysanthemum*, lily, tulip, rye grass, red clover, orchard grass, alfalfa, tall fescue, and perennial grass, but it is not limited thereto. More preferably, it is a dicot plant and even more preferably *Arabidopsis thaliana*.

According to one embodiment of the present invention, selection is made for *Arabidopsis thaliana* in which expression of human-derived FUT8 gene is introduced for exhibiting its activity in a qm plant of which expression of FucTA, FucTB, XylT and GnTII gene is removed.

The present invention further provides a callus and a seed of the above-mentioned transgenic plant.

The present invention further provides a method for producing a transgenic plant for the production of a protein containing hypoallergenic paucimannose-type N-glycan that does not include α1,3-fucose and β1,2-xylose residues but includes α1,6-fucose residue, above-mentioned method being characterized in that it includes the following steps of:

(1) preparing a quadruple mutant (qm) plant which is deficient of the functions of FucTA, FucTB, XylT and GnTII proteins and can produce a protein containing hypoallergenic paucimannose-type N-glycan that does not include α1,3-fucose and β1,2-xylose residues, and (2) transforming the quadruple mutant (qm) plant prepared in the above step (1) with a recombinant vector containing a gene encoding the human-derived α1,6-fucosyltransferase (FUT8) protein followed by overexpression of FUT8 gene, and selecting a transgenic plant which is deficient of the functions of FucTA, FucTB, XylT and GnTII proteins.

The quadruple mutant (qm) plant of the above step (1) is characterized in that it is produced by crossing the independent mutants, each deficient of the function of FucTA, FucTB, XylT and GnTII proteins and selecting a plant which produces a protein containing hypoallergenic paucimannose-type N-glycan that does not include α1,3-fucose and β1,2-xylose residues.

As for the method for determining the plant deficient of the function of FucTA, FucTB, XylT and GnTII in the above step (1) according to one embodiment of the present invention, to select a line in which expression of the FucTA, FucTB, XylT or GnTII gene is eliminated or significantly suppressed due to insertion of one T-DNA specifically to the FucTA, FucTB, XylT or GnTII gene, a plant inserted with T-DNA can be selected by a method in which segregation ratio of herbicide or antibiotics resistance is analyzed on a selection medium, or presence of a mutant gene in a genomic DNA of a transgenic plant or insertion of T-DNA is analyzed based on PCR using a primer pair specific to FucTA, FucTB, XylT and GnTII gene and T-DNA. Furthermore, based on gene expression analysis using reverse transcription (RT) PCR, a homozygote line of *Arabidopsis thaliana* in which T-DNA is inserted into both sets of the homologous chromosomes of a transformant can be selected.

Furthermore, with regard to the method for determining a plant which exhibits the activity of α1,6-fucosyltransferase (FUT8) according to insertion of human-derived FUT8 gene in the above step (2) of one embodiment of the present invention, it is also possible that, to select a line exhibiting the expression of FUT8 gene, segregation ratio of herbicide or antibiotics resistance on a selection medium can be analyzed, or insertion of FUT8 gene present in a genomic DNA of a transgenic plant can be analyzed by using a primer pair specific to FUT8 gene, and thus a transgenic plant can be selected. Furthermore, expression of the above gene can be also analyzed by RT-PCR.

The present invention further provides a transgenic plant prepared by the aforementioned method to produce proteins containing hypoallergenic paucimannose-type N-glycan that does not include α1,3-fucose and β1,2-xylose residues but includes α1,6-fucose residue.

As for the method for analyzing N-glycan based on deficient function of FucTA, FucTB, XylT and GnTII and expression of FUT8 gene in the transgenic plant according to one embodiment of the present invention, immunoblotting and affinoblotting analysis can be included. Function of FucTA, FucTB, XylT, GnTII and FUT8 can be analyzed by any method which is well known in the art, and preferably, the analysis can be made by performing immunoblotting for detecting peptides containing plant-specific monosaccharides and complex type N-glycan using α1,3-fucose, β1,2-xylose antibodies (each diluted at 1:10000, Agrisera), HRP (horseradish peroxidase) antibody (diluted at 1:10000, Sigma) or affinoblotting for detecting mannose type N-glycan using ConA (Concanavalin A) (Sigma), for detecting N-acetylglucosamine type (GlcNAc type) N-glycan using GS-II (*Griffonia simplicifolia*) (Molecular probes) lectins, and for detecting N-glycan containing α1,6-fucose using LCA (*Lens culinaris*) (USBiological) lectin. Alternatively, the analysis can be made by whole N-glycan profiling based on MALDI-TOF mass analysis after digesting the whole N-glycan by peptide: N-glycanase A (PNGase A).

For the above immunoblotting and affinoblotting, enzymes like horseradish peroxidase (HRP), alkali phosphatase, β-galactosidase, urease, catalase, glucooxidase, lactic acid dehydrognease, amylase, biotin-avidin complex, or the like can be used. For fluorescent immunoassay, a fluorescent material or a fluorophore like fluorescein isothiocyanate, tetramethyl rhodaimine isothiocyanate, substituted rhodaimine isothiocyanate, dichlorotriazine isothiocyanate, Alexa, and AlexaFluoro can be used. For radioactive immunoassay, a radioisotope such as tritium, iodine, phosphorus, or sulfur can be used. For luminescent immunoassay, a luciferase method, a lumunol peroxidase POD method, and the like can be used with a luminescent material like dioxetan compound. Like the case of using an avidin-biotin method or streptoavidin-biotin method, an antibody may be conjugated to a labeling material, if necessary. For conjugation between a labeling material and an antibody, a glutaraldehyde method, a maleimide method, a pyridyl sulfide method, or a periodic acid method can be used in case of an enzyme-linked immunoassay. For radioactive immunoassay, a chloramine T method, a Bolton-Hunter method, or the like can be used.

Examples of the immunoassay method include, in addition to the above four kinds of the method, an immunoprecipitation method, an immunoturbidimetric method, a Western blotting method, an immunostaining method, an immunodiffusion method or the like. However, it is not limited to them, any immunoblotting method that is generally used in the pertinent art is included.

The method for purifying and analyzing the aforementioned protein having N-glycan can be confirmed by a method well known in the art. Examples of the well-known method include any method which is well known in the art like chromatography, electrophoresis, and mass analysis. It preferably includes HPLC (high performance liquid chromatography) profiling and MALDI-TOF (matrix-assisted laser desorption/ionization) mass analysis, but not limited thereto.

The present invention further provides a method for producing a protein containing hypoallergenic paucimannose-type N-glycan that does not include α1,3-fucose and β1,2-xylose residues but includes α1,6-fucose residue, including a step of expressing a gene encoding an exogenous glycoprotein in the aforementioned plants.

Expression of a gene encoding a foreign glycoprotein in the above-mentioned plant can be carried out by transforming a plant with a recombinant vector which comprises gene encoding a foreign glycoprotein.

Examples of the foreign glycoprotein include human β-glucocerebrosidase, erythropoietin (EPO), human growth hormone (hGH), hepatitis B vaccine, insulin, interleukin, interferon, platelet derived growth factor, hemoglobin, elastin, collagen, fibroblast growth factor, human growth factor, human serum albumin, colony simulation factor (CSFs), and an antibody, but it is not limited thereto.

The aforementioned method for producing glycoproteins includes steps of expressing a protein having hypoallergenic paucimannose-type N-glycan in a tissue or a cell of a plant and isolating and purifying the expressed foreign glycoproteins. However, the method is not limited to them, and a method well known in the art is also included.

Purification of the expressed foreign glycoproteins can be carried out by using salting-out, dialysis, chromatography, electrophoresis, or ultracentrifuge. In case of high handling scale, a method of separating proteins with different solubility by centrifugational process after modifying salt concentration or pH is generally used (i.e., salting-out). Furthermore, it is also possible to have ion chromatography which utilizes a difference in electrostatic interaction in proteins, filtration chromatography in which separation is made based on size or shape of protein molecules, affinity chromatography in which specific intermolecular interaction is utilized, or ultracentrifuge in which biomaterials are separated based on density gradient of sugar or the like in a solution by utilizing a difference in precipitation rate against centrifugal force. However, the method is not limited to them, and any common methods that are well known in the art are all included.

The present invention further provides a protein containing hypoallergenic paucimannose-type N-glycan that does not include α1,3-fucose and β1,2-xylose residues but includes α1,6-fucose residue. Above-mentioned protein can be produced by the aforementioned method.

The present invention still further provides a pharmaceutical composition comprising the aforementioned protein as an active ingredient. The pharmaceutical composition has a meaning which is similar to that of biopharmaceuticals, and it indicates a pharmaceutical product including protein, a hormone, a vaccine or the like that is produced by a living cell using a recombinant DNA technique and used for diagnosis, prophylaxis, and therapeutics.

Herein below, the present invention is explained in greater detail in view of the Examples. However, it is evident that the following Examples are given only for exemplification of the present invention and, by no means, the present invention is limited to the following Examples.

EXAMPLES

Figure 3:
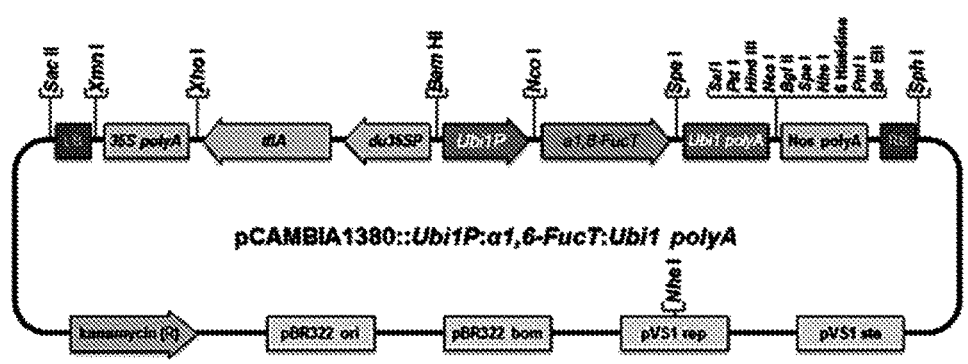
FIG. 3 shows a gene map and restriction enzyme sites of a binary vector for introducing human-derived FUT8 gene to the qm plant.

Example 1. Construction of Binary Vector for Expression of Human-Derived FUT8 Gene To introduce FUT8 gene for the α1,6-fucosyltransferase (FUT8) activity, cDNA encoding FUT8 gene was isolated from human cDNA library based on a PCR method using the primers of SEQ ID NOS: 26 and 27 (see, Table 2), and the nucleotide sequence was analyzed by sequencing. The FUT8 gene was used to prepare a gene construct that constitutively express the FUT8 under the regulation of Ubiquitin 1 promoter (Ubi1P). Furthermore, by introducing the gene construct to a binary vector which includes toxoflavin lyase (tflA) gene as a toxoflavin resistant selection marker was used to make FUT8 expression construct. The results are shown in FIG. 2 and FIG. 3.

Figure 4:
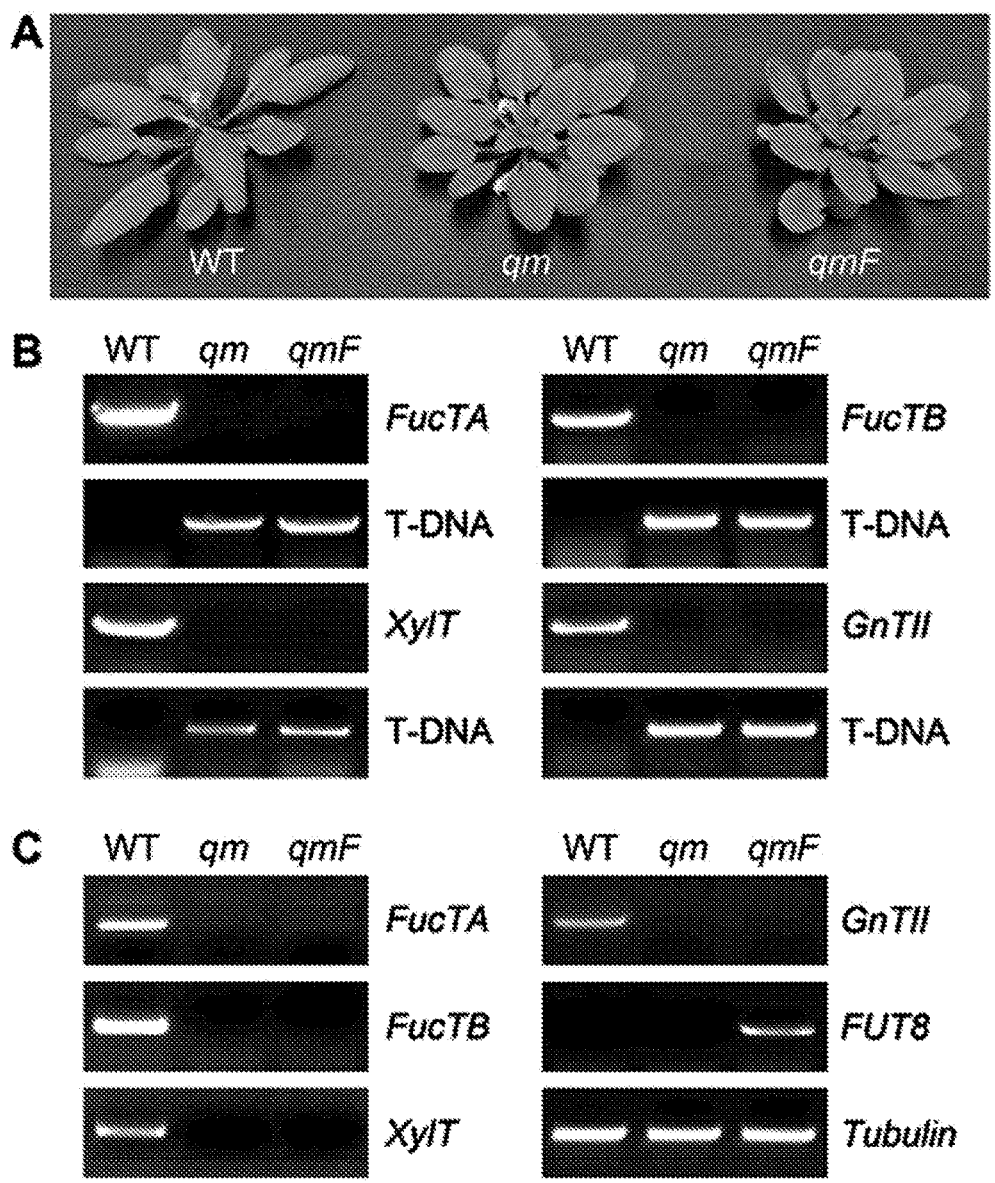
FIGS. 4A, 4B, and 4C show a quadruple mutant (qm) having completely lost or severely suppressed gene functions due to insertion of T-DNA into *Arabidopsis thaliana* FucTA, FucTB, XylT and GnTII genes, and a qmF plant in which human-derived FUT8 gene is introduced into the qm plant to express α1,6-fucosyltransferase (FUT8) activity.

Example 2. Preparation of Plant Quadruple Mutant (Qm) which is Deficient of Function of *Arabidopsis thaliana* FucTA, FucTB, XylT, GnTII Gene by T-DNA Insertion and qmF Plant Introduced with Human-Derived FUT8 Gene 1. Plant Materials and Growth Conditions Sterilized seeds of *Arabidopsis thaliana* WT (*Arabidopsis thaliana* Col-0), qm and qmF plants were grown on a MS medium containing salt mixture supplemented with 3% sucrose and 0.25% gelatin gum. They were cultivated at 22° C. and 70% humidity conditions in a growth chamber having supplemental lighting (dark period for 8 hours/light period for 16 hours; 120 µmol m$^{-2}$ sec$^{-1}$). A difference in the phenotype of the above plants is shown in FIG. 4A.

2. Preparation of qmF Plant by Introducing FUT8 Gene

The binary vector constructed in Example 1 was introduced into the qm plant by using *Agrobacterium tumefaciens*. The transformed heterozygous qmF plant was selected by utilizing the toxoflavin resistance which is exhibited by tflA gene included in the binary vector. Transgenic plants containing a single copy of the transgene were confirmed by Mendel's segregation ratio based on toxoflavin resistance. The results are shown in the following Table 1.

TABLE 1

| Line | Total | Resistance | Sensitivity | $\chi^2$ |
|---|---|---|---|---|
| 4 | 100 | 74 | 23 | 0.05 |
| 6 | 100 | 82 | 18 | 2.61 |

As shown in Table 1, the ratio of daughter plants of the heterozygous qmF plant line was determined on a medium containing toxoflavin. Based on a $\chi^2$ test, copy number of T-DNA insertion was determined, and the significance level of $\chi^2$ test for Line 4 and Line 6 was 0.05 and 2.61, respectively. The daughter plants obtained from the qmF plant line which has been confirmed to have a single copy of FUT8 gene was again subjected to the resistance test using a medium containing toxoflavin. Accordingly, a homozygous qmF plant was obtained.

3. Genotyping of Inserted Sequence

Seeds of each of *Arabidopsis thaliana* having T-DNA insertion in the FucTA, FucTB, XylT, and GnTII gene were obtained from T-DNA insertion mutant collection of *Arabidopsis* Biological Resource Center. To select homozygous *Arabidopsis thaliana* line, in which T-DNA is inserted into both sets of the homologous chromosomes, PCR and reverse transcription polymerase chain reaction (RT-PCR) using the primer pairs of Table 2 were carried out. Each of the selected homozygous mutant was used to make a quadruple (i.e., FucTA, FucTB, XylT, and GnTII genes) mutant by crossing. Based on genotyping, a homozygous quadruple mutant (qm) plant in which a T-DNA is inserted into the FucTA, FucTB, XylT, GnTII genes, respectively, was selected. The results are shown in FIG. 4B.

For the genotyping, genomic DNA was extracted from the leaves of *Arabidopsis thaliana* by using phenol-chloroform. Based on PCR using a combination of primers specific to each gene (see, Table 2), insertion site of T-DNA and homozygous property were determined. PCR conditions are as follows; 1 cycle, 2 minutes at 95° C. (denaturation); 30 cycles, 20 seconds at 95° C. (denaturation), 40 seconds at 58° C. (annealing), 1 minute at 72° C. (elongation); and 1 cycle, 5 minutes at 72° C. The PCR was performed by using e-Taq DNA polymerase mixture (SolGent).

4. Expression Analysis of FucTA, FucTB, XylT, GnTII and FUT8 Gene Using Reverse Transcription Polymerase Chain Reaction Total RNAs were extracted from leaf tissues of *Arabidopsis thaliana* according to the protocols of NucleoSpin RNA Plant Kit (Macherey-Nagel). Extracted total RNA was used to prepare cDNA by using ReverTraAce-α kit (Toyobo). 1 µl of single stranded cDNA was used as a template for subsequent PCR. To determine the expression of each of FucTA, FucTB, XylT, GnTII and FUT8 gene, forward primers and reverse primers that are described in Table 2 were used. Tubulin primer was used as a control of RNA content. PCR conditions are as follows; 1 cycle, 2 minutes at 95° C. (denaturation); 30 cycles, 20 seconds at 95° C. (denaturation), 40 seconds at 58° C. (annealing), 1 minute at 72° C. (elongation); and 1 cycle, 5 minutes at 72° C. The PCR was performed by using e-Taq DNA polymerase mixture (SolGent).

TABLE 2

Primers used in the present invention

| Primer | Nucleotide sequence (5'→3') | Use |
|---|---|---|
| FucTA-F | GAGGAGGCAAAAATTACATGTATATGC TCATCC (SEQ ID NO: 11) | Genotyping |
| FucTA-R | CAGCGACTAGAGATTGGAAGAACTTCT CTGTG (SEQ ID NO: 11) | Genotyping, RT-PCR |
| FucTB-F | TGTCTCCGGTACAGCCAAAAACTGAGA G (SEQ ID NO: 13) | Genotyping, RT-PCR |

TABLE 2-continued

Primers used in the present invention

| Primer | Nucleotide sequence (5'→3') | Use |
|---|---|---|
| FucTB-R | AAGCAGCAGGGTTAGCTGCGAGATACT T (SEQ ID NO: 14) | Genotyping, RT-PCR |
| XylT-F | CACAGAGAGGAATGATGGAATCTTCAG CTT (SEQ ID NO: 15) | Genotyping |
| XylT-R | ATTCAACATCTCATCATTCACCAGCCG (SEQ ID NO: 16) | Genotyping, RT-PCR |
| GnTII-F | GGTGGATGATGAACACTGTATGGGATG G (SEQ ID NO: 17) | Genotyping |
| GnTII-R | TCATGGAGATGCACTGCTACTGCTGTA AC (SEQ ID NO: 18) | Genotyping, RT-PCR |
| FucTA-LB | GCGTGGACCGCTTGCTGCAACT (SEQ ID NO: 19) | Genotyping |
| FucTB-LB | CCCATTTGGACGTGAATGTAGACAC (SEQ ID NO: 20) | Genotyping |
| XylT-LB | GCCTTTTCAGAAATGGATAAATAGCCT TGCTTC (SEQ ID NO: 21) | Genotyping |
| GnTII-LB | TGTGCCAGGTGCCCACGGAATAG (SEQ ID NO: 22) | Genotyping |
| FucTA-RTF | ATGGGTGTTTTCTCCAATCTTCGAGGT (SEQ ID NO: 23) | RT-PCR |
| XylT-RTF | ATGAGTAAACGGAATCCGAAGATTCTG AA (SEQ ID NO: 24) | RT-PCR |
| GnTII-RTF | ATGGCAAATCTTTGGAAGAAGCAGA (SEQ ID NO: 25) | RT-PCR |
| FUT8-F | CCATGGCAATTACTGTCTCATTAGTGA ACAAT (SEQ ID NO: 26) | RT-PCR |
| FUT8-R | ACTAGTTATTTCTCAGCCTCAGGATAT GTGGG (SEQ ID NO: 27) | Cloning, RT-PCR |
| Tubulin-F | ATCGATTCCGTTCTCGATGT (SEQ ID NO: 28) | Cloning, RT-PCR |
| Tubulin-R | ATCCAGTTCCTCCTCCCAAC (SEQ ID NO: 29) | RT-PCR |

Example 3. Analysis and Determination of N-Glycan of WT, Qm and qmF Plants Using Immunoblotting and Affinoblotting For immunoblotting and affinoblotting analyses, total proteins were extracted from 3-week old WT, qm and qmF plants. Total proteins extract were separated by 10% SDS-PAGE, and transferred to a nitrocellulose membrane (Hybond-ECL, Amersham). To determine the N-glycan having plant-specific sugar residues by immunoblotting, the membrane was labeled with an antibody against α1,3-fucose, β1,2-xylose (Agrisera) or HRP (Sigma). Furthermore, to measure the N-glycan of high-mannose type and N-glycan with GlcNAc terminal by affinoblotting, ConA (Sigma) and GS-II lectin (Molecular Probes) were used, respectively. Furthermore, to determine the N-glycan having α1,6-fucose sugar residue by affinoblotting, LCA lectin (USBiological), which mainly recognizes a peptide having N-glycan including mannose residue but shows significantly increased affinity when the N-glycan includes α1,6-fucose residue, was used.

In order to confirm whether or not the *Arabidopsis thaliana* qm plant produces a protein containing customized paucimannose-type N-glycan that does not include α1,3-fucose and β1,2-xylose residues and to see whether or not the qmF plant produces a protein containing customized paucimannose-type N-glycan which includes humanized α1,6-fucose sugar residue, the inventors of the present invention conducted immunoblotting using anti-HRP, anti-fucose, and anti-xylose antibodies and affinoblotting analysis using ConA, GS-II, and LCA. The results are shown in FIG. 5.

Figure 5:
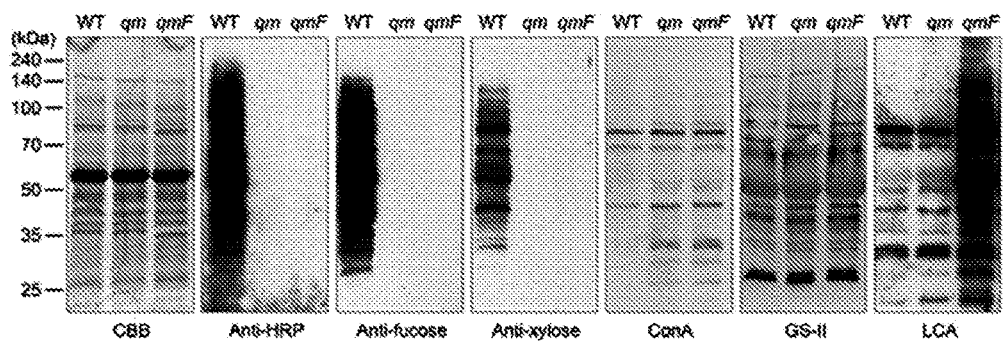
FIG. 5 N-glycan structure of WT, qm and qmF plants were analyzed by using immunoblotting and affinoblotting analysis; CBB: Coomassie brilliant blue (CBB) stain, Anti-HRP: immunoblotting using horseradish peroxidase (HRP: specifically binds to peptide which has an N-glycan containing α1,3-fucose and β1,2-xylose residues) antibody, Anti-fucose: immunoblotting using an antibody specific to a peptide which has an N-glycan containing α1,3-fucose residue, Anti-xylose: immunoblotting using an antibody specific to a peptide which has an N-glycan containing β1,2-xylose residue, ConA: affinoblotting using Concanavalin A (ConA: lectin specific to a peptide which has an N-glycan containing mannose or glucose residue in the middle or at non-reducing terminal), GSII: affinoblotting using lectin isolated from a seed of *Griffonia simplicifolia*, which is tropical African legume plant (lectin specifically binds to a peptide which has an N-glycan containing α- or β-GlcNAc residue at non-reducing terminal), and LCA: affinoblotting using *Lens Culinaris* Agglutinin (LCA: strongly binds to a peptide which has an N-glycan containing a non-reducing terminal α-mannose residue and a core α1,6-fucose residue).

As shown in FIG. 5, anti-HRP, anti-fucose, and anti-xylose antibodies show a response only to the protein derived from the WT plant, and show no response to the protein derived from the qm and qmF plant. These results indicate that paucimannose-type and complex type N-glycan including α1,3-fucose and β1,2-xylose residues are not synthesized in the qm and qmF plant. On the contrary, ConA showed a strong response to the protein isolated from the qm and qmF plant but showed a weak response to the protein isolated from the WT. In the case of GS-II, almost the same response was shown in the wild type, the qm and qmF plant. These results indicate that the amount of mannose type N-glycan is increased in the qm and qmF plant.

Furthermore, in the case of LCA which mainly recognizes a peptide having N-glycan including mannose residue but shows significantly increased affinity when N-glycan includes α1,6-fucose residue, a weak response to the protein isolated from the WT and qm plant was shown, while a particularly strong response to the qmF plant was shown. These results indicate that the amount of customized hypoallergenic paucimannose-type N-glycan including humanized α1,6-fucose residue is specifically increased in the qmF plant.

Example 4. Analysis and Determination of N-Glycan of WT, Qm and qmF Plant Using Matrix-Assisted Laser Desorption/Ionization Time-of-Flight Mass Spectrometry (MALDI-TOF MS)

1. Separation, Purification, and Permethylation of N-Glycan

Proteins for purification of N-glycan were extracted from the WT, qm and qmF plant by using the method of Bakker, et. al. (Bakker et. al., 2006, Proc. Natl. Acad. Sci. USA, 103:7577-7582). The proteins were degraded by using trypsin, and fixed N-glycan was released by using PNGase A (Peptide N-Glycosidase A) (Prozyme, USA). The sample was allowed to pass through a C18 Sep-Pak cartridge followed by freeze drying. The carbohydrate fractions were dissolved in dimethyl sulfoxide (DMSO) and subjected to permethylation according to the method of Anumula and Taylor (Anumula and Taylor, 1992, Aanl. Biochem. 203: 101-108).

2. Matrix-Assisted Laser Desorption/Ionization Time-of-Flight Mass Spectrometry (MALDI-TOF MS) Analysis MALDI-TOF MS was carried out by the inventors of the present invention, in which the analysis was performed in a reflector positive ion mode by using 20 mg m$^{-1}$ dihydroxybenzoic acid (DHBA) in a 50% (v/v) methanol solution. The spectrum was obtained by using LTQ XL (Thermo Fisher Scientific Inc.).

To obtain quantitative and structure comparative information, the glycoproteins extracted from the plant were used for MALDI-TOF MS. The results are shown in FIG. 6 to FIG. 9.

Figure 6:
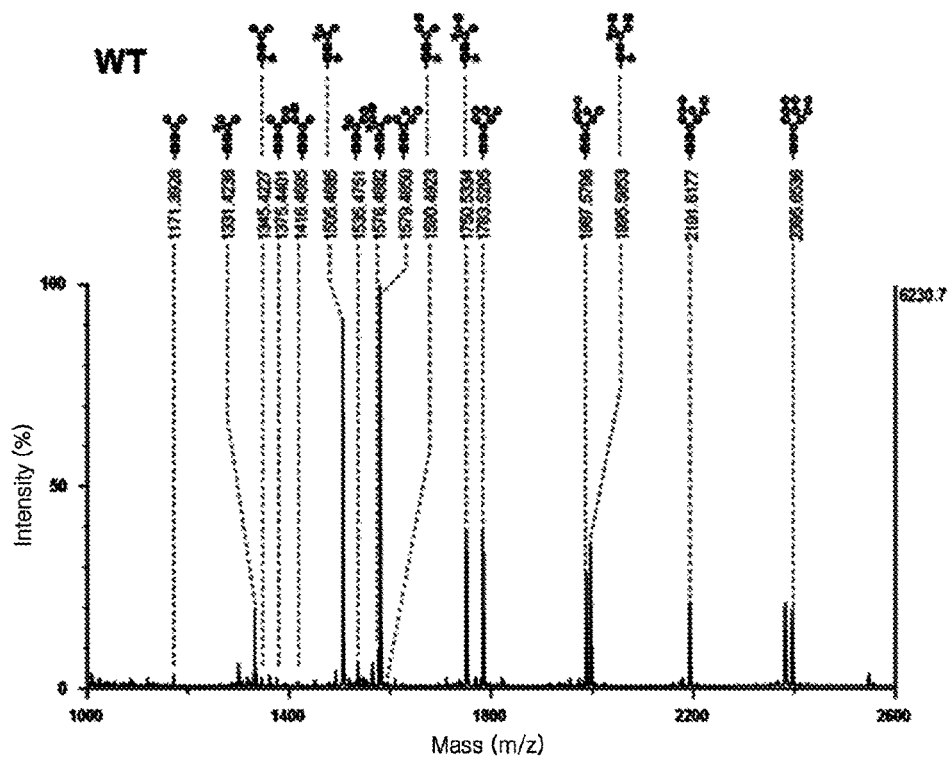
FIG. 6 N-glycan structure of a wild type (WT) plant was analyzed by using MALDI-TOF mass spectrometry. It was found that the proteins isolated from the WT plant mainly contain a high-mannose type N-glycan with $Man_5GlcNAc_2$ (m/z 1579.44850) structure and paucimannose-type N-glycan with $Man_3XylFucGlcNAc_2$ (m/z 1505.4685) structure containing plant-specific β1,2-xylose and α1,3-fucose residues.
Figure 7:
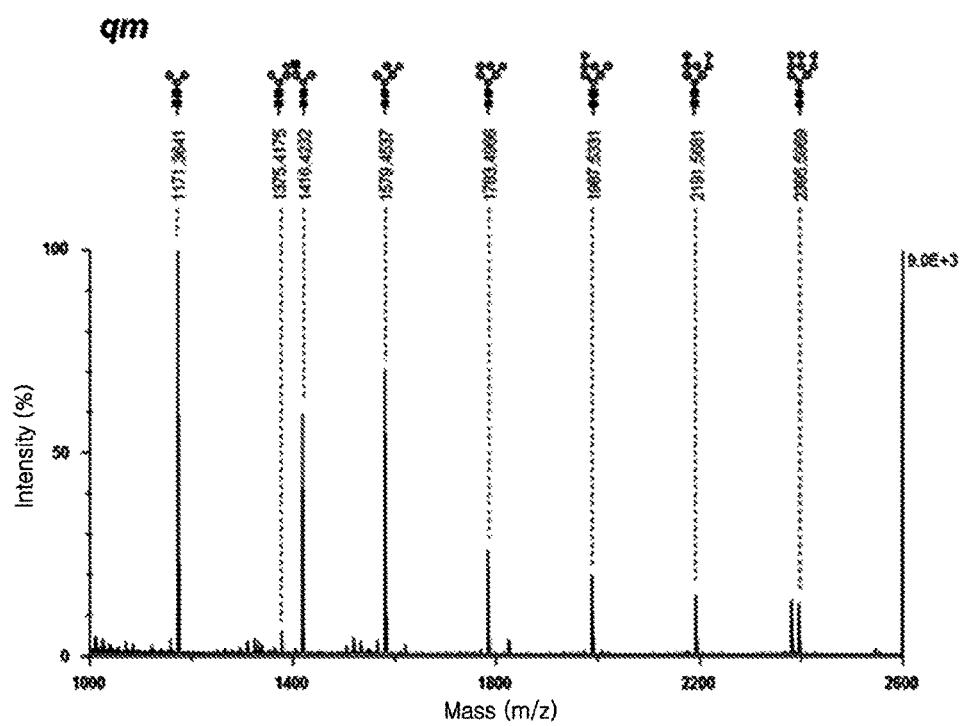
FIG. 7 N-glycan structure of a qm plant was analyzed by using MALDI-TOF mass spectrometry. It was found that the proteins isolated from qm plant mainly contain paucimannose-type N-glycan with $Man_3GlcNAc_2$ (m/z 1171.3641) structure in which plant-specific β1,2-xylose and α1,3-fucose residue are absent, and contain high-mannose type N-glycan with $Man_5GlcNAc_2$ (m/z 1579.4537) structure.
Figure 8:
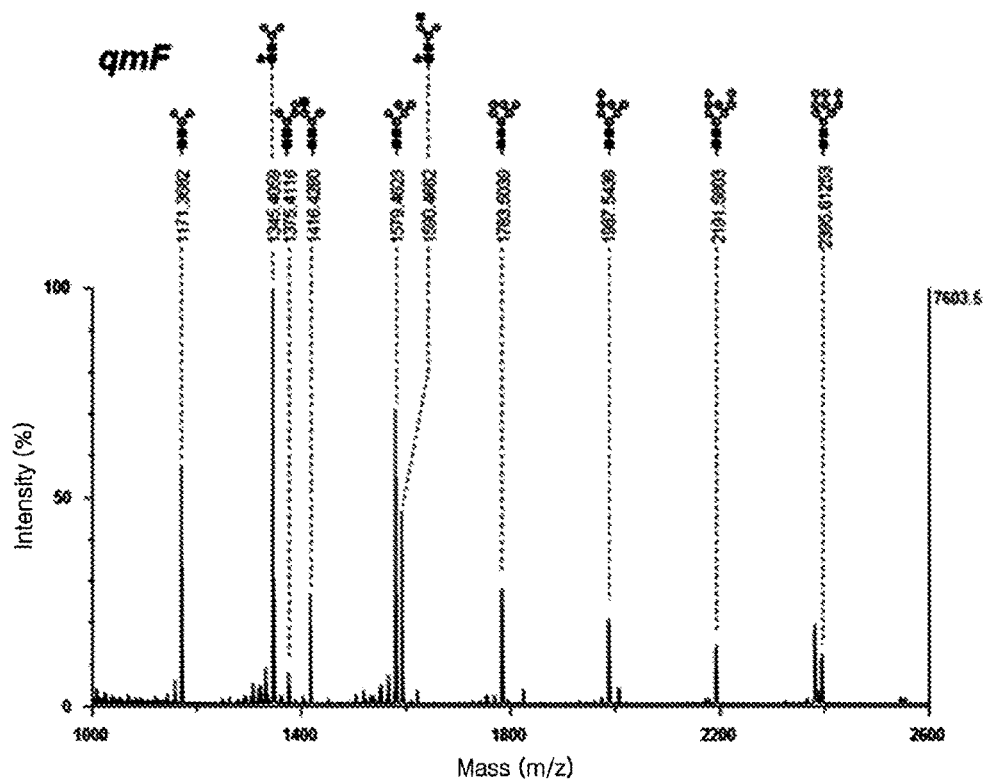
FIG. 8 N-glycan structure of a qmF plant was analyzed by using MALDI-TOF mass spectrometry. It was found that the proteins isolated from qmF plant mainly contain hypoallergenic paucimannose-type N-glycan with $Man_3GlcNAc[Fuc(α1,6)]GlcNAc$ (m/z 1345.4059) structure containing α1,6-fucose residue and high-mannose type N-glycan with $Man_5GlcNAc_2$ (m/z 1579.4623) structure, while N-glycan containing plant-specific β1,2-xylose and α1,3-fucose residue is absent.

The mass spectrum of the N-glycan obtained from the WT shows that high-mannose type N-glycan and N-glycan with various structures including α1,3-fucose and β1,2-xylose residues are produced in the WT (FIG. 6). The mass spectrum of the N-glycan obtained from the qm plant shows that paucimannose and complex type N-glycan including α1,3-fucose and β1,2-xylose residues are not produced in the qm plant, while paucimannose-type and high-mannose type N-glycan not including α1,3-fucose and β1,2-xylose are mainly produced therein (FIG. 7). Meanwhile, the mass spectrum of the N-glycan obtained from the qmF plant shows that paucimannose-type and high-mannose type N-glycan including α1,6-fucose residue are mainly produced while plant-specific paucimannose-type N-glycan including α1,3-fucose and β1,2-xylose residues is not produced (FIG. 8).

TABLE 3

| Measured m/z | N-glycan structure | WT (%) | qm (%) | qmF (%) |
|---|---|---|---|---|
| 1171.3928 | Man$_3$GlcNAc$_2$ | 0.64 | 26.57 | 12.22 |
| 1331.4238 | Man$_3$XylGlcNAc$_2$ | 3.50 | ND | ND |
| 1345.4227 | Man$_3$FucGlcNAc$_2$ | 0.54[a] | ND | 23.32[b] |
| 1375.4401 | Man$_4$GlcNAc$_2$ | 0.53 | 1.64 | 1.61 |
| 1416.4695 | GlcNAcMan$_3$GlcNAc$_2$ | 0.35 | 17.57 | 6.15 |
| 1505.4685 | Man$_3$XylFucGlcNAc$_2$ | 19.15 | ND | ND |
| 1535.4751 | Man$_4$XylGlcNAc$_2$ | 1.54 | ND | ND |
| 1576.4882 | GlcNAcMan$_3$XylGlcNAc$_2$ | 1.97 | ND | ND |
| 1579.4950 | Man$_5$GlcNAc$_2$ | 21.90 | 24.54 | 19.72 |
| 1590.4923 | GlcNAcMan$_3$FucGlcNAc$_2$ | 0.51[c] | ND | 12.54[d] |
| 1750.5334 | GlcNAcMan$_3$XylFucGlcNAc$_2$ | 9.64 | ND | ND |
| 1783.5295 | Man$_6$GlcNAc$_2$ | 9.43 | 9.36 | 8.10 |
| 1987.5796 | Man$_7$GlcNAc$_2$ | 7.93 | 8.22 | 6.89 |
| 1995.5853 | GlcNAc$_2$Man$_3$XylFucGlcNAc$_2$ | 10.40 | ND | ND |
| 2191.6177 | Man$_8$GlcNAc$_2$ | 6.11 | 6.50 | 4.82 |
| 2395.6563 | Man$_9$GlcNAc$_2$ | 5.86 | 5.60 | 4.63 |
| | Total | 100 | 100 | 100 |

Figure 9:
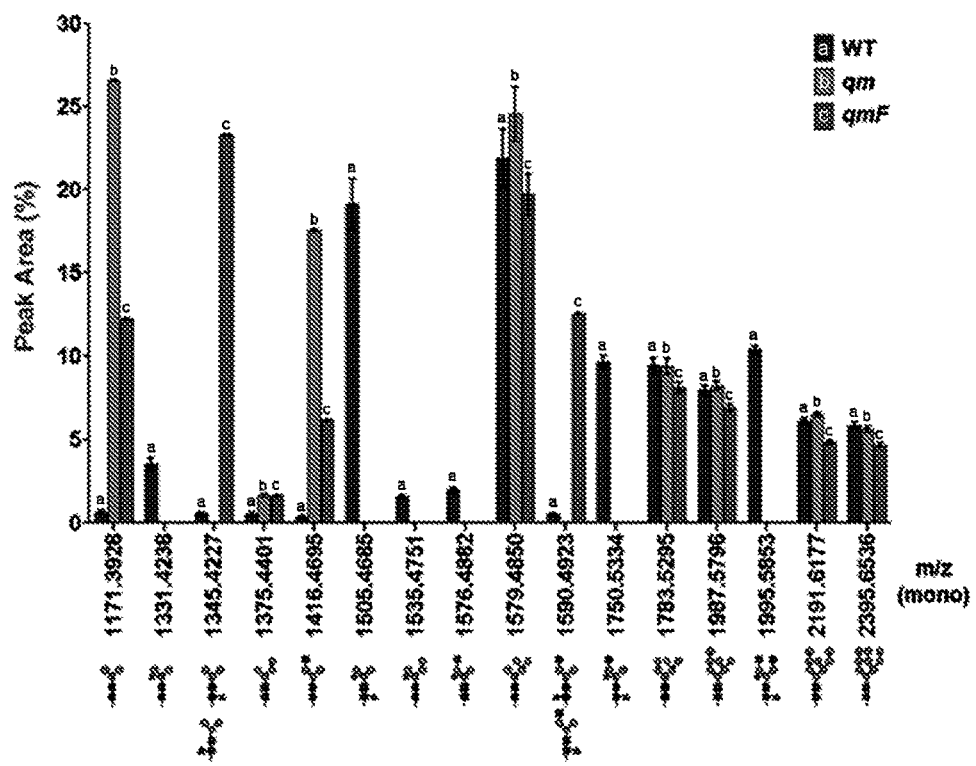
FIG. 9 shows the relative amount (area ratio: peak area %) of N-glycan of each structure present in the WT, qm and qmF plants.

[a]Man$_3$FucGlcNAc$_2$ = Man$_3$GlcNAc[Fuc(α1,3)]GlcNAc,
[b]Man$_3$FucGlcNAc$_2$ = Man$_3$GlcNAc[Fuc(α1,6)]GlcNAc,
[c]GlcNAcMan$_3$FucGlcNAc$_2$ = GlcNAcMan$_3$GlcNAc[Fuc(α1,3)]GlcNAc,
[d]GlcNAcMan$_3$FucGlcNAc$_2$ = GlcNAcMan$_3$GlcNAc[Fuc(α1,6)]GlcNAc;
ND, not detected; Man, mannose; Xyl, xylose; GlcNAc, N-acetylglycosamine; Fuc, fucose; Gal, galactose The above Table 3 shows the MALDI-TOF MS analysis result of the N-glycan which has been obtained from the WT, qm and qmF plants. The above numerical values indicate the relative amount of N-glycan with each structure (area ratio: peak area %). The results are shown in FIG. 9.

As a quantitative analysis of N-glycan obtained from the WT, qm and qmF plants, MALDI-TOF mass analysis was carried out by using the N-glycan which has been produced as a derivative according to the permethylation before the analysis. To obtain favorable ion statistics, the provided spectrum was generated from various spectrums of 100 laser shots. The integrated peak area of the whole radioisotope element group was measured based on relative quantitative analysis.

Taken together the above test results, it was confirmed by the inventors of the present invention that deficient function of core α1,3-fucosyltransferase A (FucTA), core α1,3-fucosyltransferase B (FucTB), β1,2-xylosyltransferase (XylT), and jβ1,2-N-acetylglucosaminyltransferase II (GnTII) in *Arabidopsis thaliana* enables complete inhibition of the production of plant-specific N-glycan in the Golgi complex, and a defect in the production of plant-specific N-glycan leads to accumulation of paucimannose-type N-glycan with Man$_3$GlcNAc$_2$ structure. Furthermore, by introducing human-derived α1,6-fucosyltransferase (FUT8) gene into the qm plant and having continuous expression of the gene therein, it was confirmed that customized hypoallergenic paucimannose-type N-glycan (Man$_3$GlcNAc[Fuc(α1,6)]GlcNAc) having α1,6-fucose is accumulated as a main product.

What is claimed is:

1. A quadruple mutant (qm) *Arabidopsis* plant having mutations that knock_out each of four endogenous genes and expressing a gene encoding an α1,6-fucosyltransferase (FUT8) protein consisting of SEQ ID NO: 10 to produce a protein containing a paucimannose-type-N-glycan that does not include α1,3-fucose and β1,2-xylose residues, but include an α1,6-fucose reside, wherein the four endogenous genes are:
the α1,3-fucosyltransferase A (FucTA) gene encoding an α1,3-fucosyltransferase A (FucTA) consisting of SEQ ID NO: 2;
the α1,3-fucosyltransferase B (FucTB) gene encoding an α1,3-fucosyltransferase B (FucTB) consisting of SEQ ID NO: 4;
the β1,2-xylosyltransferase (XylT) gene encoding a β1,2-xylosyltransferase (XylT) consisting of SEQ ID NO: 6; and
the β1,2-N-acetylglucosaminyltransferase II (GnTII) gene encoding a β1,2-N-acetylglucosaminyltransferase II (GnTII) consisting of SEQ ID NO: 8.

2. The quadruple mutant *Arabidopsis* plant of claim 1, wherein a part or all of each nucleotide sequence of the FucTA gene, the FucTB gene, the XylT gene, and the GnTII gene is deleted, or a T-DNA is inserted into each nucleotide sequence of the FucTA gene, the FucTB gene, the XylT gene, and the GnTII gene of the quadruple mutant *Arabidopsis* plant.

3. The quadruple mutant (qm) *Arabidopsis* plant of claim 1, wherein the mutations of the FucTA gene, the FucTB gene, the XylT gene, and the GnTII gene are achieved by one or more selected from the group consisting of genome modification, gene deletion, gene insertion, T-DNA insertion, homologous recombination, and transposon tagging.

4. The quadruple mutant *Arabidopsis* plant of claim 1, wherein the FucTA protein is encoded by a cDNA having the nucleotide sequence represented by SEQ ID NO: 1;
the FucTB protein is encoded by a cDNA having the nucleotide sequence represented by SEQ ID NO: 3;
the XylT protein is encoded by a cDNA having the nucleotide sequence represented by SEQ ID NO: 5; and
the GnTII protein is encoded by a cDNA having the nucleotide sequence represented by SEQ ID NO: 7.

5. The quadruple mutant *Arabidopsis* plant of claim 1 being a transgenic plant, in which a transgene encoding the α1,6-fucosyltransferase (FUT8) protein is incorporated into the genome of the quadruple mutant *Arabidopsis* plant of claim 1.

6. The transgenic plant of claim 5, wherein the paucimannose-type N-glycan is Man₃GlcNAc[Fuc(α1,6)]GlcNAc.

7. The transgenic plant of claim 5, wherein the incorporation of the gene encoding the α1,6-fucosyltransferase (FUT8) protein is carried out by transforming with a recombinant vector which comprises the gene encoding the α1,6-fucosyltransferase (FUT8) protein consisting of the amino acid sequence of SEQ ID NO: 10.

8. The transgenic plant of claim 7, wherein the recombinant vector comprises a polynucleotide having an *Arabidopsis thaliana* ubiquitin 1 promoter operably linked to a nucleic acid encoding the α1,6-fucosyltransferase (FUT8) protein consisting of the amino acid sequence of SEQ ID NO: 10, and an *Arabidopsis thaliana* ubiquitin 1 polyadenylation signal operably linked to the nucleic acid.

9. The transgenic plant of claim 5, wherein the transgenic plant is selected from the group consisting of rice, wheat, barley, corn, soybean, potato, red bean, oat, sorghum, *Arabidopsis thaliana*, Chinese cabbage, daikon, pepper, strawberry, tomato, watermelon, cucumber, cabbage, oriental melon, zucchini, scallion, onion, carrot, *ginseng*, tobacco, cotton, sesame, sugar cane, sugar beet, wild sesame, peanut, canola, apple, pear, jujube, peach, kiwi, grape, tangerine, persimmon, plum, apricot, banana, rose, *gladiolus, gerbera*, carnation, *chrysanthemum*, lily, tulip, rye grass, red clover, orchard grass, alfalfa, tall fescue, and perennial grass.

10. A callus of the transgenic plant of claim 5.

11. A seed of the transgenic plant of claim 5 wherein said seed comprises said transgene.

12. A method for producing a transgenic *Arabidopsis* plant for production of a protein containing a paucimannose-type N-glycan that does not include α1,3-fucose and β1,2-xylose residues but includes an α1,6-fucose residue, the method comprising:
preparing a quadruple mutant (qm) *Arabidopsis* plant having mutations that knock_out each of four endogenous genes to produce a protein containing a paucimannose-type N-glycan that does not include α1,3-fucose and β1,2-xylose residues; and
transforming the quadruple mutant *Arabidopsis* plant with a recombinant vector containing a transgene encoding the α1,6-fucosyltransferase (FUT8) consisting of SEQ ID NO: 10 to overexpress the FUT8 gene
wherein the four endogenous genes are:
the α1,3-fucosyltransferase A (FucTA) gene encoding an α1,3-fucosyltransferase A (FucTA) consisting of SEQ ID NO: 2;

the α1,3-fucosyltransferase B (FucTB) gene encoding an α1,3-fucosyltransferase B (FucTB) consisting of SEQ ID NO: 4;

the β1,2-xylosyltransferase (XylT) gene encoding a β1,2-xylosyltransferase (XylT) consisting of SEQ ID NO: 6; and the β1,2-N-acetylglucosaminyltransferase II (GnTII) gene encoding a β1,2-N-acetylglucosaminyltransferase II (GnTII) consisting of SEQ ID NO: 8.

13. The method of claim 12, wherein preparation of the quadruple mutant (qm) *Arabidopsis* plant comprises crossing independent mutants, each having a mutation that knocks out a separate one of the four endogenous genes, and selecting a plant for producing the protein containing a paucimannose-type N-glycan that does not include α1,3-fucose and β1,2-xylose residues.

14. A method of using the transgenic plant of claim 5 for producing a protein containing the paucimannose-type N-glycan that does not include α1,3-fucose and β1,2-xylose residues but includes the α1,6-fucose residue, the method comprising expressing a gene encoding the protein in the transgenic plant of claim 5.

15. The method of claim 14, wherein the expression of the gene is carried out by transforming the plant with a recombinant vector comprising the gene encoding the protein.

16. The method of claim 14, further comprising purifying the expressed protein.

17. The method of claim 16, wherein the purification of the protein is carried out by one or more selected from the group consisting of salting-out, dialysis, chromatography, electrophoresis, and ultracentrifuge.

\* \* \* \* \*

SEQUENCE LISTING

<160> NUMBER OF SEQ ID NOS: 30

<210> SEQ ID NO 1
<211> LENGTH: 1332
<212> TYPE: DNA
<213> ORGANISM: Arabidopsis thaliana

<400> SEQUENCE: 1

```
atgggtgttt tctccaatct tcgaggtcct aaaattggat tgacccatga agaattgcct      60
gtagtagcca atggctctac ttcttcttct tcgtctcctt cctcttttcaa gcgtaaagtc     120 tcgaccttttt tgccaatctg cgtggctctt gtcgtcatta tcgagatcgg gttcctctgt     180
cggctcgata acgcttcttt ggtcgatacg ttaacccatt tttcaccaa gtcgtcgtcc       240 gatttgaaag ttgggtcagg aatagagaaa tgccaggagt ggttagagag agtggattca     300
gttacttatt ctagagattt cactaaagat ccgatttta tctctggtag taacaaggac       360
```

```
ttcaaatcgt gctctgttga ttgtgtaatg ggattcactt cagataagaa acctgatgcg    420
gcttttggat taagtcatca acctggaaca ctcagtataa tccgttccat ggaatcagca    480
cagtattacc aagagaataa tcttgctcaa gctcttgaag ccttaatgaa gacgaatgtt    540
aagattgatt cttatggtgg ttgtcaccgg aatcgggatg ggagtgtgga gaaggttgaa    600
gctcttaagc actacaaatt cagtctagct tttgagaaca ccaacgagga ggattatgtc    660
acagagaagt tcttccaatc tctagtcgct ggatctgtcc ctgtggttgt tggagctcca    720
aatatagaag aatttgcacc ttctcctgac tcattccttc acattaagca gatggatgat    780
gtcaaggcag ttgcaaagaa aatgaagtat cttgcggata ccctgacgc ctataatcag    840 acgctaagat ggaaacatga aggccttca gattcttta aggcacttat tgatatggct    900
gctgtacact cttcttgtcg tctctgcatc tttgtggcta caaggattcg tgagcaagaa    960
gagaagagcc ctgagtttaa gagacgaccc tgcaaatgca ccagaggctc agagacagtt   1020
tatcatttgt atgttagaga aagaggacgg tttgacatgg aatccatctt cttgaaggat   1080
ggaaatctga ctctggaagc tctggaatct gcggttcttg cgaagttcat gtctctgaga   1140
tatgaaccaa tatggaagaa ggaaagaccc gcgagcttaa gaggagacgg caagcttaga   1200
gtacatggga tatatcctat tggtctgact caaagacaag ctctttacaa cttcaaattc   1260
gaaggaaatt caagtctcag tactcacata cagagaaacc cttgtcccaa attcgaagtt   1320
gtctttgtct aa                                                       1332
```

<210> SEQ ID NO 2
<211> LENGTH: 443
<212> TYPE: PRT
<213> ORGANISM: Arabidopsis thaliana

<400> SEQUENCE: 2

```
Met Gly Val Phe Ser Asn Leu Arg Gly Pro Lys Ile Gly Leu Thr His
1               5                   10                  15

Glu Glu Leu Pro Val Val Ala Asn Gly Ser Thr Ser Ser Ser Ser Ser
            20                  25                  30

Pro Ser Ser Phe Lys Arg Lys Val Ser Thr Phe Leu Pro Ile Cys Val
        35                  40                  45

Ala Leu Val Val Ile Ile Glu Ile Gly Phe Leu Cys Arg Leu Asp Asn
    50                  55                  60

Ala Ser Leu Val Asp Thr Leu Thr His Phe Phe Thr Lys Ser Ser Ser
65                  70                  75                  80

Asp Leu Lys Val Gly Ser Gly Ile Glu Lys Cys Gln Glu Trp Leu Glu
                85                  90                  95

Arg Val Asp Ser Val Thr Tyr Ser Arg Asp Phe Thr Lys Asp Pro Ile
            100                 105                 110

Phe Ile Ser Gly Ser Asn Lys Asp Phe Lys Ser Cys Ser Val Asp Cys
        115                 120                 125

Val Met Gly Phe Thr Ser Asp Lys Lys Pro Asp Ala Ala Phe Gly Leu
    130                 135                 140

Ser His Gln Pro Gly Thr Leu Ser Ile Ile Arg Ser Met Glu Ser Ala
145                 150                 155                 160

Gln Tyr Tyr Gln Glu Asn Asn Leu Ala Gln Ala Leu Glu Ala Leu Met
                165                 170                 175

Lys Thr Asn Val Lys Ile Asp Ser Tyr Gly Gly Cys His Arg Asn Arg
            180                 185                 190
```

Asp Gly Ser Val Glu Lys Val Glu Ala Leu Lys His Tyr Lys Phe Ser
            195                 200                 205

Leu Ala Phe Glu Asn Thr Asn Glu Glu Asp Tyr Val Thr Glu Lys Phe
    210                 215                 220

Phe Gln Ser Leu Val Ala Gly Ser Val Pro Val Val Gly Ala Pro
225                 230                 235                 240

Asn Ile Glu Glu Phe Ala Pro Ser Pro Asp Ser Phe Leu His Ile Lys
                245                 250                 255

Gln Met Asp Asp Val Lys Ala Val Ala Lys Lys Met Lys Tyr Leu Ala
            260                 265                 270

Asp Asn Pro Asp Ala Tyr Asn Gln Thr Leu Arg Trp Lys His Glu Gly
        275                 280                 285

Pro Ser Asp Ser Phe Lys Ala Leu Ile Asp Met Ala Ala Val His Ser
    290                 295                 300

Ser Cys Arg Leu Cys Ile Phe Val Ala Thr Arg Ile Arg Glu Gln Glu
305                 310                 315                 320

Glu Lys Ser Pro Glu Phe Lys Arg Arg Pro Cys Lys Cys Thr Arg Gly
                325                 330                 335

Ser Glu Thr Val Tyr His Leu Tyr Val Arg Glu Arg Gly Arg Phe Asp
            340                 345                 350

Met Glu Ser Ile Phe Leu Lys Asp Gly Asn Leu Thr Leu Glu Ala Leu
        355                 360                 365

Glu Ser Ala Val Leu Ala Lys Phe Met Ser Leu Arg Tyr Glu Pro Ile
    370                 375                 380

Trp Lys Lys Glu Arg Pro Ala Ser Leu Arg Gly Asp Gly Lys Leu Arg
385                 390                 395                 400

Val His Gly Ile Tyr Pro Ile Gly Leu Thr Gln Arg Gln Ala Leu Tyr
                405                 410                 415

Asn Phe Lys Phe Glu Gly Asn Ser Ser Leu Ser Thr His Ile Gln Arg
            420                 425                 430

Asn Pro Cys Pro Lys Phe Glu Val Val Phe Val
        435                 440

<210> SEQ ID NO 3
<211> LENGTH: 1542
<212> TYPE: DNA
<213> ORGANISM: Arabidopsis thaliana

<400> SEQUENCE: 3
atgggtgttt tctcgaatct tcgaggaccc agagccggag ctacccacga tgaatttccg      60
gcgaccaatg gctctccttc gtcttcttct tctccatctt catcaatcaa gcgaaaatta     120
tcgaatttgt taccactctg cgttgctctg gtagttatcg ctgagatcgg gtttctgggt     180
cggctcgata aagtcgcttt ggttgatacg ttgactgatt tcttcaccca gtctccgtca     240
ctctcgcagt ctccaccggc gagatccgat cggaagaaga tcggattatt tactgatagg     300
agctgcgagg agtggttgat gagagaagat tcagttactt actctagaga ttttactaaa     360
gatccaattt ttatctctgg tggtgaaaag gactttcaat ggtgttctgt ggattgtaca     420
tttggagata gttcagggaa acaccagatg ctgcgtttg gattaggtca gaaacctgga     480
actcttagta taatacgttc catggaatca gcacagtatt atccagaaaa tgatcttgca     540
caggcacgac ggagaggtta tgatatagtg atgaccacta gtctatcatc agatgttcct     600
gttggatatt tttcgtgggc ggagtatgat attatgtctc cggtacagcc aaaaactgag     660
agagctattg cagctgcttt tatttctaat tgtggtgctc ggaattttcg tctacaagca     720

-continued

```
cttgaggcat tgatgaaaac taacattaag attgattctt atggtggttg tcatcgaaac    780
cgggatggga aagttgacaa ggttgaagct cttaagcgat acaaattcag tttggctttt    840
gagaatacta acgaggaaga ttatgtcacc gagaagttct ttcaatcctt agttgctggg    900
tccgtcccg tggtagttgg tcctccaaat atagaagaat tgcgcctgc ttcggactca    960
ttccttcaca ttaagactat ggaagatgta gagccagttg caaagagaat gaagtatctc   1020
gcagctaacc ctgctgctta taatcagaca ctaagatgga aatacgaggg tccttcagat   1080
tctttcaagg cacttgttga tatggctgct gtacactctt cttgccgtct ctgcattttc   1140
ctggccacga gggtccgaga caagaagag gaaagcccta atttcaagaa acgaccgtgc    1200
aaatgtagca ggggaggatc agacacagtt tatcatgttt tgttagaga aagaggccgg    1260
tttgaaatgg aatcagtctt tttgagggggt aaaagtgtga ctcaggaagc tctagaatct   1320
gcagttctcg ccaagttcaa gtctttaaaa catgaggcag tgtggaagaa ggaaaggcct   1380
ggaaacttaa aaggagacaa agagcttaaa atacatcgga tttacccgct tggcctaacg   1440
caacgacagg ctttgtacaa cttcaaattc gagggaaatt cgagtctaag tagtcacatt   1500
caaaacaacc cttgtgctaa atttgaggtt gtcttcgtct ag                     1542
```

<210> SEQ ID NO 4
<211> LENGTH: 513
<212> TYPE: PRT
<213> ORGANISM: Arabidopsis thaliana

<400> SEQUENCE: 4

```
Met Gly Val Phe Ser Asn Leu Arg Gly Pro Arg Ala Gly Ala Thr His
1               5                   10                  15

Asp Glu Phe Pro Ala Thr Asn Gly Ser Pro Ser Ser Ser Ser Ser Pro
            20                  25                  30

Ser Ser Ser Ile Lys Arg Lys Leu Ser Asn Leu Leu Pro Leu Cys Val
        35                  40                  45

Ala Leu Val Val Ile Ala Glu Ile Gly Phe Leu Gly Arg Leu Asp Lys
    50                  55                  60

Val Ala Leu Val Asp Thr Leu Thr Asp Phe Phe Thr Gln Ser Pro Ser
65                  70                  75                  80

Leu Ser Gln Ser Pro Ala Arg Ser Asp Arg Lys Lys Ile Gly Leu
            85                  90                  95

Phe Thr Asp Arg Ser Cys Glu Glu Trp Leu Met Arg Glu Asp Ser Val
            100                 105                 110

Thr Tyr Ser Arg Asp Phe Thr Lys Asp Pro Ile Phe Ile Ser Gly Gly
        115                 120                 125

Glu Lys Asp Phe Gln Trp Cys Ser Val Asp Cys Thr Phe Gly Asp Ser
    130                 135                 140

Ser Gly Lys Thr Pro Asp Ala Ala Phe Gly Leu Gly Gln Lys Pro Gly
145                 150                 155                 160

Thr Leu Ser Ile Ile Arg Ser Met Glu Ser Ala Gln Tyr Tyr Pro Glu
            165                 170                 175

Asn Asp Leu Ala Gln Ala Arg Arg Gly Tyr Asp Ile Val Met Thr
        180                 185                 190

Thr Ser Leu Ser Ser Asp Val Pro Val Gly Tyr Phe Ser Trp Ala Glu
    195                 200                 205

Tyr Asp Ile Met Ser Pro Val Gln Pro Lys Thr Glu Arg Ala Ile Ala
210                 215                 220
```

```
Ala Ala Phe Ile Ser Asn Cys Gly Ala Arg Asn Phe Arg Leu Gln Ala
225                 230                 235                 240

Leu Glu Ala Leu Met Lys Thr Asn Ile Lys Ile Asp Ser Tyr Gly Gly
            245                 250                 255

Cys His Arg Asn Arg Asp Gly Lys Val Asp Lys Val Glu Ala Leu Lys
        260                 265                 270

Arg Tyr Lys Phe Ser Leu Ala Phe Glu Asn Thr Asn Glu Glu Asp Tyr
    275                 280                 285

Val Thr Glu Lys Phe Phe Gln Ser Leu Val Ala Gly Ser Val Pro Val
290                 295                 300

Val Val Gly Pro Pro Asn Ile Glu Glu Phe Ala Pro Ala Ser Asp Ser
305                 310                 315                 320

Phe Leu His Ile Lys Thr Met Glu Asp Val Glu Pro Val Ala Lys Arg
            325                 330                 335

Met Lys Tyr Leu Ala Ala Asn Pro Ala Ala Tyr Asn Gln Thr Leu Arg
        340                 345                 350

Trp Lys Tyr Glu Gly Pro Ser Asp Ser Phe Lys Ala Leu Val Asp Met
    355                 360                 365

Ala Ala Val His Ser Ser Cys Arg Leu Cys Ile Phe Leu Ala Thr Arg
370                 375                 380

Val Arg Glu Gln Glu Glu Ser Pro Asn Phe Lys Lys Arg Pro Cys
385                 390                 395                 400

Lys Cys Ser Arg Gly Gly Ser Asp Thr Val Tyr His Val Phe Val Arg
            405                 410                 415

Glu Arg Gly Arg Phe Glu Met Glu Ser Val Phe Leu Arg Gly Lys Ser
        420                 425                 430

Val Thr Gln Glu Ala Leu Glu Ser Ala Val Leu Ala Lys Phe Lys Ser
    435                 440                 445

Leu Lys His Glu Ala Val Trp Lys Lys Glu Arg Pro Gly Asn Leu Lys
450                 455                 460

Gly Asp Lys Glu Leu Lys Ile His Arg Ile Tyr Pro Leu Gly Leu Thr
465                 470                 475                 480

Gln Arg Gln Ala Leu Tyr Asn Phe Lys Phe Glu Gly Asn Ser Ser Leu
            485                 490                 495

Ser Ser His Ile Gln Asn Asn Pro Cys Ala Lys Phe Glu Val Val Phe
        500                 505                 510

Val
```

<210> SEQ ID NO 5
<211> LENGTH: 1605
<212> TYPE: DNA
<213> ORGANISM: Arabidopsis thaliana

<400> SEQUENCE: 5

```
atgagtaaac ggaatccgaa gattctgaag attttctgt atatgttact tctcaactct     60
ctctttctca tcatctactt cgttttcac tcatcgtcgt tttcaccgga gcagtcacag    120
cctcctcata taccacgt ttcagtgaat aaccaatcgg cgattcagaa accgtggccg     180
atcttacctt cttacctccc atggacgccg ccgcagagga atctaccaac tggctcctgc    240
gaaggttact tcgggaatgg atttacaaag agagttgact tccttaagcc gaggattgga    300
ggaggaggag aaggaagctg gttccgatgt tttacagtg agacattaca gagttcgatt    360
tgtgaaggaa ggaatctgag aatggttccg gatcggattg ttatgtcgag aggaggtgag    420
aagttagagg aagttatggg gaggaaagag gaggaggagc ttcctgcgtt tcgacaaggt    480
```

-continued

```
gcgtttgagg tagcggaaga ggtttcttca cggttaggtt ttaagagaca ccgtcgtttt    540
ggtggaggag aaggaggtag tgcggtttct cggcggctgg tgaatgatga gatgttgaat    600
gaatatatgc aagaaggtgg aattgataga catacaatga gagatttggt tgcttcgatt    660
cgtgctgttg ataccaatga tttcgtttgt gaagagtggg tggaggaacc gaccttgctt    720
gtcactagat tcgagtacgc aaatctcttc catactgtga cagattggta tagtgcctat    780
gtttcgtcta gagtcaccgg tttgcctaat cgacctcacg ttgttttcgt tgacggacac    840
tgcacgacgc agctagaaga aacatggaca gctttgtttt ccggaatcag atacgcaaag    900
aacttcacca accggttttg tttccgccac gcgattcttt caccattggg atacgaaacc    960
gctcttttta aaggcttgtc cggagaaata gactgcaagg gagattcagc tcacaatctg   1020
tggcaaaacc cggacgataa aaggactgcg aggatatcag agtttggtga aatgatcaga   1080
gcagctttcg ggttgcctgt caatagacac cgctcattag aaaagccgct atcatcatca   1140
tcatcatcag cctcagttta taatgttctt tttgtccgcc gtgaagatta cttagcccat   1200
cctcgtcatg gcggtaaagt ccagtctcgg ctcatcaatg aggaagaagt gttcgactcg   1260
ttgcatcatt gggttgcaac tgggtccacc ggtctgacca aatgcgggat taaccttgtg   1320
aatggcttgc ttgcacacat gtcaatgaaa gatcaagtcc gagccattca agatgcttca   1380
gtgatcatag gagctcatgg agcaggactg actcacattg tctctgcaac accaaacaca   1440
acgatatttg agataataag cgtcgagttt cagagacctc atttcgagct tatagctaag   1500
tggaaaggat tggagtatca cgcgatgcat ctggcgaact cacgagcgga accaacggct   1560
gtgattgaga agttaacgga gatcatgaag agccttggct gctaa                   1605
```

<210> SEQ ID NO 6
<211> LENGTH: 534
<212> TYPE: PRT
<213> ORGANISM: Arabidopsis thaliana

<400> SEQUENCE: 6

```
Met Ser Lys Arg Asn Pro Lys Ile Leu Lys Ile Phe Leu Tyr Met Leu
1               5                   10                  15

Leu Leu Asn Ser Leu Phe Leu Ile Ile Tyr Phe Val Phe His Ser Ser
            20                  25                  30

Ser Phe Ser Pro Glu Gln Ser Gln Pro Pro His Ile Tyr His Val Ser
        35                  40                  45

Val Asn Asn Gln Ser Ala Ile Gln Lys Pro Trp Pro Ile Leu Pro Ser
    50                  55                  60

Tyr Leu Pro Trp Thr Pro Pro Gln Arg Asn Leu Pro Thr Gly Ser Cys
65                  70                  75                  80

Glu Gly Tyr Phe Gly Asn Gly Phe Thr Lys Arg Val Asp Phe Leu Lys
                85                  90                  95

Pro Arg Ile Gly Gly Gly Gly Glu Gly Ser Trp Phe Arg Cys Phe Tyr
            100                 105                 110

Ser Glu Thr Leu Gln Ser Ser Ile Cys Glu Gly Arg Asn Leu Arg Met
        115                 120                 125

Val Pro Asp Arg Ile Val Met Ser Arg Gly Gly Glu Lys Leu Glu Glu
    130                 135                 140

Val Met Gly Arg Lys Glu Glu Glu Leu Pro Ala Phe Arg Gln Gly
145                 150                 155                 160

Ala Phe Glu Val Ala Glu Glu Val Ser Ser Arg Leu Gly Phe Lys Arg
                165                 170                 175
```

His Arg Arg Phe Gly Gly Glu Gly Ser Ala Val Ser Arg Arg
            180                 185                 190

Leu Val Asn Asp Glu Met Leu Asn Glu Tyr Met Gln Glu Gly Gly Ile
            195                 200                 205

Asp Arg His Thr Met Arg Asp Leu Val Ala Ser Ile Arg Ala Val Asp
            210                 215                 220

Thr Asn Asp Phe Val Cys Glu Glu Trp Val Glu Pro Thr Leu Leu
225                 230                 235                 240

Val Thr Arg Phe Glu Tyr Ala Asn Leu Phe His Thr Val Thr Asp Trp
            245                 250                 255

Tyr Ser Ala Tyr Val Ser Ser Arg Val Thr Gly Leu Pro Asn Arg Pro
            260                 265                 270

His Val Val Phe Val Asp Gly His Cys Thr Thr Gln Leu Glu Glu Thr
            275                 280                 285

Trp Thr Ala Leu Phe Ser Gly Ile Arg Tyr Ala Lys Asn Phe Thr Lys
            290                 295                 300

Pro Val Cys Phe Arg His Ala Ile Leu Ser Pro Leu Gly Tyr Glu Thr
305                 310                 315                 320

Ala Leu Phe Lys Gly Leu Ser Gly Glu Ile Asp Cys Lys Gly Asp Ser
            325                 330                 335

Ala His Asn Leu Trp Gln Asn Pro Asp Asp Lys Arg Thr Ala Arg Ile
            340                 345                 350

Ser Glu Phe Gly Glu Met Ile Arg Ala Ala Phe Gly Leu Pro Val Asn
            355                 360                 365

Arg His Arg Ser Leu Glu Lys Pro Leu Ser Ser Ser Ser Ser Ser Ala
            370                 375                 380

Ser Val Tyr Asn Val Leu Phe Val Arg Arg Glu Asp Tyr Leu Ala His
385                 390                 395                 400

Pro Arg His Gly Gly Lys Val Gln Ser Arg Leu Ile Asn Glu Glu Glu
            405                 410                 415

Val Phe Asp Ser Leu His His Trp Val Ala Thr Gly Ser Thr Gly Leu
            420                 425                 430

Thr Lys Cys Gly Ile Asn Leu Val Asn Gly Leu Leu Ala His Met Ser
            435                 440                 445

Met Lys Asp Gln Val Arg Ala Ile Gln Asp Ala Ser Val Ile Ile Gly
            450                 455                 460

Ala His Gly Ala Gly Leu Thr His Ile Val Ser Ala Thr Pro Asn Thr
465                 470                 475                 480

Thr Ile Phe Glu Ile Ile Ser Val Glu Phe Gln Arg Pro His Phe Glu
            485                 490                 495

Leu Ile Ala Lys Trp Lys Gly Leu Glu Tyr His Ala Met His Leu Ala
            500                 505                 510

Asn Ser Arg Ala Glu Pro Thr Ala Val Ile Glu Lys Leu Thr Glu Ile
            515                 520                 525

Met Lys Ser Leu Gly Cys
        530

<210> SEQ ID NO 7
<211> LENGTH: 1293
<212> TYPE: DNA
<213> ORGANISM: Arabidopsis thaliana

<400> SEQUENCE: 7
atggcaaatc tttggaagaa gcagagattg agagatacag gtttatgtcg tttagggatt        60

```
ctatttgctg ttactttgtc tatagttctg atgttggtgt ctgtacctag aactgctttg      120
aatggttctt ctattgacga tgatttggat ggtttagata aagatttgga agctaagctt      180
aatgcttcat tgctaagtgt agctagaggt aatagaatgt ctctaaggtt gcatagaagg      240
aaccattttt cgcctagaaa tacgatctg ttcccggatt tggcaaaaga tcgtgtggtt       300
atcgtcttgt atgtgcataa tcgggctcag tattttcgag tcacagtgga agtttgtcg       360 aaggttaaag gtaaagtga gacattgttg attgttagtc atgatggtta ctttgaagag       420
atgaatagga ttgtggagag tattaagttt tgtcaagtga aacagatttt ctcgcccttat     480 tcgcctcata tatcgtac tagcttcccg ggtgtgaccc tgaatgattg taagaacaag        540
ggtgatgagg caaaggggca ttgtgaaggt aatcctgatc agtatgggaa tcatcggtct      600
ccgaagattt tatctttgaa gcatcactgg tggtggatga tgaacactgt atgggatggg      660
ttggaagaga ctaaaggaca tgaggggcat atccttttca ttgaagaaga tcattttctg      720
tttcctaatg cctatcgtaa catacagact cttacgaggc tgaaacccgc aaagtgtcct      780
gactgttttg ctgctaattt agcaccgtct gatgtgaagt caagaggaga agggcttgaa      840
agtttggttg cagagagaat gggaaatgtt gggtattctt ttaatagaag tgtgtgggag      900
aatattcatc agaaggcaag agagttttgt ttctttgatg attacaactg ggatataacg      960
atgtgggcaa cggttttccc gtcgtttggt tccccggtgt acacattgcg agggcctagg     1020
actagtgcgg tacacttggg aaaatgtggg ttgcatcaag gtagaggaga tgagggtgat     1080
tgcatcgata atggggtcgt aaacatgaa gttaaggaaa cagataaagt tgtgaacata      1140
aaagaaggat ggggagttcg ggtgtataag catcaagcgg gttataaagc cggtttcgaa     1200
ggttggggag gttggggcga tgatagggac cgacatttat gtttggattt tgccactatg     1260
tatcgttaca gcagtagcag tgcatctcca tga                                  1293

<210> SEQ ID NO 8
<211> LENGTH: 430
<212> TYPE: PRT
<213> ORGANISM: Arabidopsis thaliana

<400> SEQUENCE: 8

Met Ala Asn Leu Trp Lys Lys Gln Arg Leu Arg Asp Thr Gly Leu Cys
1               5                   10                  15

Arg Leu Gly Ile Leu Phe Ala Val Thr Leu Ser Ile Val Leu Met Leu
                20                  25                  30

Val Ser Val Pro Arg Thr Ala Leu Asn Gly Ser Ser Ile Asp Asp Asp
        35                  40                  45

Leu Asp Gly Leu Asp Lys Asp Leu Glu Ala Lys Leu Asn Ala Ser Leu
    50                  55                  60

Leu Ser Val Ala Arg Gly Asn Arg Met Ser Leu Arg Leu His Arg Arg
65                  70                  75                  80

Asn His Phe Ser Pro Arg Asn Thr Asp Leu Phe Pro Asp Leu Ala Lys
                85                  90                  95

Asp Arg Val Val Ile Val Leu Tyr Val His Asn Arg Ala Gln Tyr Phe
            100                 105                 110

Arg Val Thr Val Glu Ser Leu Ser Lys Val Lys Gly Ile Ser Glu Thr
        115                 120                 125

Leu Leu Ile Val Ser His Asp Gly Tyr Phe Glu Glu Met Asn Arg Ile
    130                 135                 140

Val Glu Ser Ile Lys Phe Cys Gln Val Lys Gln Ile Phe Ser Pro Tyr
```

```
                145                 150                 155                 160
Ser Pro His Ile Tyr Arg Thr Ser Phe Pro Gly Val Thr Leu Asn Asp
                    165                 170                 175

Cys Lys Asn Lys Gly Asp Glu Ala Lys Gly His Cys Glu Gly Asn Pro
                    180                 185                 190

Asp Gln Tyr Gly Asn His Arg Ser Pro Lys Ile Val Ser Leu Lys His
                    195                 200                 205

His Trp Trp Trp Met Met Asn Thr Val Trp Asp Gly Leu Glu Thr
            210                 215                 220

Lys Gly His Glu Gly His Ile Leu Phe Ile Glu Glu Asp His Phe Leu
225                 230                 235                 240

Phe Pro Asn Ala Tyr Arg Asn Ile Gln Thr Leu Thr Arg Leu Lys Pro
                    245                 250                 255

Ala Lys Cys Pro Asp Cys Phe Ala Ala Asn Leu Ala Pro Ser Asp Val
                    260                 265                 270

Lys Ser Arg Gly Glu Gly Leu Glu Ser Leu Val Ala Glu Arg Met Gly
                    275                 280                 285

Asn Val Gly Tyr Ser Phe Asn Arg Ser Val Trp Glu Asn Ile His Gln
                    290                 295                 300

Lys Ala Arg Glu Phe Cys Phe Phe Asp Asp Tyr Asn Trp Asp Ile Thr
305                 310                 315                 320

Met Trp Ala Thr Val Phe Pro Ser Phe Gly Ser Pro Val Tyr Thr Leu
                    325                 330                 335

Arg Gly Pro Arg Thr Ser Ala Val His Phe Gly Lys Cys Gly Leu His
                    340                 345                 350

Gln Gly Arg Gly Asp Glu Gly Asp Cys Ile Asp Asn Gly Val Val Asn
                    355                 360                 365

Ile Glu Val Lys Glu Thr Asp Lys Val Val Asn Ile Lys Glu Gly Trp
                    370                 375                 380

Gly Val Arg Val Tyr Lys His Gln Ala Gly Tyr Lys Ala Gly Phe Glu
385                 390                 395                 400

Gly Trp Gly Gly Trp Gly Asp Asp Arg Asp Arg His Leu Cys Leu Asp
                    405                 410                 415

Phe Ala Thr Met Tyr Arg Tyr Ser Ser Ser Ala Ser Pro
                    420                 425                 430

<210> SEQ ID NO 9
<211> LENGTH: 1728
<212> TYPE: DNA
<213> ORGANISM: Artificial Sequence
<220> FEATURE:
<223> OTHER INFORMATION: cDNA sequence of FUT8 gene

<400> SEQUENCE: 9
atggggcctt ggactggttc ctggcgttgg attatgctca ttcttttttgc ctggggggacc      60 ttgctgtttt atataggtgg tcacttggta cgagataatg accatcctga tcactctagc     120
cgagaactgt ccaagattct ggcaaagctt gaacgcttaa acagcagaa tgaagacttg      180 aggcgaatgg ccgaatctct ccggatacca gaaggcccta ttgatcaggg gccagctata     240
ggaagagtac gcgttttaga agagcagctt gttaaggcca agaacagat tgaaaattac     300 aagaaacaga ccagaaatgg tctggggaag gatcatgaaa tcctgaggag gaggattgaa     360
aatggagcta agagctctg gttttttccta cagagtgaat tgaagaaatt aaagaactta     420
gaaggaaatg aactccaaag acatgcagat gaatttcttt tggattagg acatcatgaa     480
```

```
aggtctataa tgacggatct atactacctc agtcagacag atggagcagg tgattggcgg      540
gaaaaagagg ccaaagatct gacagaactg gttcagcgga gaataacata tcttcagaat      600
cccaaggact gcagcaaagc caaaaagctg gtgtgtaata tcaacaaagg ctgtggctat      660
ggctgtcagc tccatcatgt ggtctactgc ttcatgattg catatggcac ccagcgaaca      720
ctcatcttgg aatctcagaa ttggcgctat gctactggtg gatgggagac tgtatttagg      780
cctgtaagtg agacatgcac agacagatct ggcatctcca ctggacactg gtcaggtgaa      840
gtgaaggaca aaaatgttca agtggtcgag cttcccattg tagacagtct tcatccccgt      900
cctccatatt tacccttggc tgtaccagaa gacctcgcag atcgacttgt acgagtgcat      960
ggtgaccctg cagtgtggtg ggtgtctcag tttgtcaaat acttgatccg cccacagcct     1020
tggctagaaa agaaaataga agaagccacc aagaagcttg gcttcaaaca tccagttatt     1080
ggagtccatg tcagacgcac agacaaagtg ggaacagaag ctgccttcca tcccattgaa     1140
gagtacatgg tgcatgttga agaacatttt cagcttcttg cacgcagaat gcaagtggac     1200
aaaaaaagag tgtatttggc cacagatgac ccttctttat taaaggaggc aaaaacaaag     1260
taccccaatt atgaatttat tagtgataac tctatttcct ggtcagctgg actgcacaat     1320
cgatacacag aaaattcact tcgtggagtg atcctggata tacattttct ctctcaggca     1380
gacttcctag tgtgtacttt ttcatcccag gtctgtcgag ttgcttatga aattatgcaa     1440
acactacatc ctgatgcctc tgcaaacttc cattctttag atgacatcta ctattttggg     1500
ggccagaatg cccacaatca aattgccatt tatgctcacc aaccccgaac tgcagatgaa     1560
attcctatgg aacctggaga tatcattggt gtggctggaa atcattggga tggctattct     1620
aaaggtgtca acaggaaatt gggaaggacg ggcctatatc cctcctacaa agttcgagag     1680
aagatagaaa cggtcaagta ccccacatat cctgaggctg agaaataa                  1728
```

<210> SEQ ID NO 10
<211> LENGTH: 575
<212> TYPE: PRT
<213> ORGANISM: Artificial Sequence
<220> FEATURE:
<223> OTHER INFORMATION: mutated FUT8 of Homo sapiens

<400> SEQUENCE: 10

```
Met Gly Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Pro Ala Ile
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Thr Arg Asn Gly Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys Asn Leu Glu Gly Asn Glu
    130                 135                 140
```

```
Leu Gln Arg His Ala Asp Glu Phe Leu Leu Asp Leu Gly His His Glu
145                 150                 155                 160

Arg Ser Ile Met Thr Asp Leu Tyr Tyr Leu Ser Gln Thr Asp Gly Ala
            165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Lys
            195                 200                 205

Lys Leu Val Cys Asn Ile Asn Lys Gly Cys Gly Tyr Gly Cys Gln Leu
        210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
            245                 250                 255

Thr Val Phe Arg Pro Val Ser Glu Thr Cys Thr Asp Arg Ser Gly Ile
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
            325                 330                 335

Arg Pro Gln Pro Trp Leu Glu Lys Glu Ile Glu Ala Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
    370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Ser Leu Leu Lys Glu
            405                 410                 415

Ala Lys Thr Lys Tyr Pro Asn Tyr Glu Phe Ile Ser Asp Asn Ser Ile
        420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Ile Tyr Ala
            500                 505                 510

His Gln Pro Arg Thr Ala Asp Glu Ile Pro Met Glu Pro Gly Asp Ile
        515                 520                 525

Ile Gly Val Ala Gly Asn His Trp Asp Gly Tyr Ser Lys Gly Val Asn
    530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
```

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
gaggaggcaa aaattacatg tatatgctca tcc                                    33

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
cagcgactag agattggaag aacttctctg tg                                     32

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
tgtctccggt acagccaaaa actgagag                                          28

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
aagcagcagg gttagctgcg agatactt                                          28

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
cacagagagg aatgatggaa tcttcagctt                                        30

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
attcaacatc tcatcattca ccagccg                                           27

<210> SEQ ID NO 17
<211> LENGTH: 28
<212> TYPE: DNA
<213> ORGANISM: Artificial Sequence
<220> FEATURE:
<223> OTHER INFORMATION: primer

<400> SEQUENCE: 17
ggtggatgat gaacactgta tgggatgg                                    28

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
tcatggagat gcactgctac tgctgtaac                                   29

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gcgtggaccg cttgctgcaa ct                                          22

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
cccatttgga cgtgaatgta gacac                                       25

<210> SEQ ID NO 21
<211> LENGTH: 33
<212> TYPE: DNA
<213> ORGANISM: Artificial Sequence
<220> FEATURE:
<223> OTHER INFORMATION: primer

<400> SEQUENCE: 21 gcctttcag aaatggataa atagccttgc ttc                               33

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
tgtgccaggt gcccacggaa tag                                         23

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
atgggtgttt tctccaatct tcgaggt                                     27

```
<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
atgagtaaac ggaatccgaa gattctgaa                                      29

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
atggcaaatc tttggaagaa gcaga                                          25

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
ccatggcaat tactgtctca ttagtgaaca at                                  32

<210> SEQ ID NO 27
<211> LENGTH: 32
<212> TYPE: DNA
<213> ORGANISM: Artificial Sequence
<220> FEATURE:
<223> OTHER INFORMATION: primer

<400> SEQUENCE: 27
actagttatt tctcagcctc aggatatgtg gg                                  32

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
atcgattccg ttctcgatgt                                                20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
atccagttcc tcctcccaac                                                20

<210> SEQ ID NO 30
<211> LENGTH: 2798
<212> TYPE: DNA
<213> ORGANISM: Artificial Sequence
<220> FEATURE:
<223> OTHER INFORMATION: Ubi1P:FUT8:Ubi1 polyA gene sequence
```

<400> SEQUENCE: 30

```
ggatccaatt ttgtaatatc ccgggatatt tcacaaattg aacatagact acagaatttt      60
agaaaacaaa ctttctctct cttatctcac ctttatcttt tagagagaaa aagttcgatt     120
tccggttgac cggaatgtat ctttgttttt tttgttttgt aacatatttc gttttccgat     180
ttagatcgga tctccttttc cgttttgtcg gaccttcttc cggtttatcc ggatctaata     240
atatccatct tagacttagc taagtttgga tctgtttttt ggttagctct tgtcaatcgc     300
ctcatcatca gcaagaaggt gaaattttg acaaataaat cttagaatca tgtagtgtct     360
ttggaccttg ggaatgatag aaacgatttg ttatagctac tctatgtatc agaccctgac     420
caagatccaa caatctcata ggttttgtgc atatgaaacc ttcgactaac gagaagtggt     480
cttttaatga gagagatatc taaaatgtta tcttaaaagc ccactcaaat ctcaaggcat     540
aaggtagaaa tgcaaatttg gaaagtgggc tgggcctttt gtggtaaagg cctgtaacct     600
agcccaatat tagcaaaacc ctagacgcgt acattgacat atataaaccc gcctcctcct     660
tgtttagggt ttctacgtga gagaagacga acacaaacc atgggccctt ggactggttc      720
ctggcgttgg attatgctca ttcttttttgc ctgggggacc ttgctgtttt ataggtgg     780
tcacttggta cgagataatg accatcctga tcactctagc cgagaactgt ccaagattct     840
ggcaaagctt gaacgcttaa aacagcagaa tgaagacttg aggcgaatgg ccgaatctct     900
ccggatacca gaaggcccta ttgatcaggg gccagctata ggaagagtac gcgttttaga     960
agagcagctt gttaaggcca agaacagat tgaaaattac aagaaacaga ccagaaatgg     1020
tctggggaag gatcatgaaa tcctgaggag gaggattgaa aatggagcta agagctctg      1080
gttttttccta cagagtgaat tgaagaaatt aaagaactta gaaggaaatg aactccaaag     1140
acatgcagat gaatttcttt tggatttagg acatcatgaa aggtctataa tgacggatct     1200
atactacctc agtcagacag atggagcagg tgattggcgg gaaaaagagg ccaaagatct     1260
gacagaactg gttcagcgga gaataacata tcttcagaat cccaaggact gcagcaaagc     1320
caaaaagctg gtgtgtaata tcaacaaagg ctgtggctat ggctgtcagc tccatcatgt     1380
ggtctactgc ttcatgattg catatggcac ccagcgaaca ctcatcttgg aatctcagaa     1440
ttggcgctat gctactggtg gatgggagac tgtatttagg cctgtaagtg agacatgcac     1500
agacagatct ggcatctcca ctggacactg gtcaggtgaa gtgaaggaca aaaatgttca     1560
agtggtcgag cttcccattg tagacagtct tcatccccgt cctccatatt tacccttggc     1620
tgtaccagaa gacctcgcag atcgacttgt acgagtgcat ggtgaccctg cagtgtggtg     1680
ggtgtctcag tttgtcaaat acttgatccg cccacagcct tggctagaaa agaaatagaa     1740
agaagccacc aagaagcttg gcttcaaaca tccagttatt ggagtccatg tcagacgcac     1800
agacaaagtg ggaacagaag ctgccttcca tcccattgaa gagtacatgg tgcatgttga     1860
agaacattttt cagcttcttg cacgcagaat gcaagtggaa aaaaaagag tgtatttggc     1920
cacagatgac ccttctttat taaaggaggc aaaaacaaag taccccaatt atgaatttat     1980
tagtgataac tctatttcct ggtcagctgg actgcacaat cgatacacag aaaattcact     2040
tcgtggagtg atcctggata tacattttct ctctcaggca gacttcctag tgtgtacttt     2100
ttcatcccag gtctgtcgag ttgcttatga aattatgcaa acactacatc ctgatgcctc     2160
tgcaaacttc cattctttag atgacatcta ctattttggg ggccagaatg cccacaatca     2220
aattgccatt tatgctcacc aaccccgaac tgcagatgaa attcctatgg aacctggaga     2280
```

```
tatcattggt gtggctggaa atcattggga tggctattct aaaggtgtca acaggaaatt   2340
gggaaggacg ggcctatatc cctcctacaa agttcgagag aagatagaaa cggtcaagta   2400
ccccacatat cctgaggctg agaaataact agtatcaaga atcccatctc ttgcttgctt   2460 tttttgttg tcttcccttt gatagggttt gtttttcttg tttcagtgac tttctatgtt    2520
aaaagataat gtcagtaaaa ggatttggtt ttctattatt ctgaatcgat tacggaagat   2580
tcttgcttaa ttccaatcta tacaagtatc gtgaaataat gaccgtttat gtgattagga   2640
gacgtgtttc attaataaaa tataagatca atacattgtt agtagtgata aactatgtac   2700
aaattgtatt gattgtaaaa gaaacacaat aggttccttt tttctacaat atattgtgac   2760
agactctctg ttttaacgaa tgaattaaat ttgtcgac                          2798
```